(12) United States Patent
Peterson et al.

(10) Patent No.: US 9,801,313 B2
(45) Date of Patent: Oct. 24, 2017

(54) UNDERWATER CONTAINER COOLING VIA INTEGRATED HEAT EXCHANGER

(71) Applicant: Microsoft Technology Licensing, LLC, Redmond, WA (US)

(72) Inventors: Eric C. Peterson, Woodinville, WA (US); Benjamin F. Cutler, Seattle, WA (US); Norman Ashton Whitaker, Jr., Clyde Hill, WA (US); Peter Johnson, Camillus, NY (US); Alexander Jacques Fleming, San Francisco, CA (US); David Bazeley Tuckerman, Lafayette, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 154 days.

(21) Appl. No.: 14/752,669

(22) Filed: Jun. 26, 2015

(65) Prior Publication Data

US 2016/0381840 A1    Dec. 29, 2016

(51) Int. Cl.
| | | |
|---|---|---|
| *H05K 7/20* | (2006.01) | |
| *G06F 1/20* | (2006.01) | |
| *F24F 5/00* | (2006.01) | |
| *F28D 15/00* | (2006.01) | |
| *H05K 7/14* | (2006.01) | |

(52) U.S. Cl.
CPC ....... *H05K 7/20836* (2013.01); *F24F 5/0046* (2013.01); *F28D 15/00* (2013.01); *G06F 1/20* (2013.01); *H05K 7/1497* (2013.01); *H05K 7/2079* (2013.01); *H05K 7/20236* (2013.01); *H05K 7/20745* (2013.01)

(58) Field of Classification Search
CPC . H05K 7/20836; H05K 7/2079; F24F 5/0046; F28D 15/00; G06F 1/20
See application file for complete search history.

(56) References Cited

U.S. PATENT DOCUMENTS 3,648,767 A * 3/1972 Balch ................. F24J 3/086
                                                    165/104.19
4,411,213 A   10/1983 Laukien
(Continued)

FOREIGN PATENT DOCUMENTS

CN    102455086 A    5/2012
DE    102011115657    3/2013
(Continued)

OTHER PUBLICATIONS

Office Action dated Jul. 29, 2016 cited in U.S. Appl. No. 14/272,676.
(Continued)

*Primary Examiner* — David M Sinclair
*Assistant Examiner* — Robert Brown
(74) *Attorney, Agent, or Firm* — Workman Nydegger

(57) ABSTRACT

In one example, a portion of a shell includes a shell wall portion that has an interior wall portion and an exterior wall portion located near the interior wall portion. In addition, fluid passageways are disposed between the interior wall portion and the exterior wall portion. One or more of the fluid passageways are defined in part by one or both of the interior wall portion and the exterior wall portion. The fluid passageways form part of heat exchanger that is integrated in the shell.

28 Claims, 18 Drawing Sheets

(56) References Cited

U.S. PATENT DOCUMENTS

| | | | |
|---|---|---|---|
| 5,263,538 A | 11/1993 | Amidieu et al. | |
| 6,145,584 A * | 11/2000 | Baynes | F28D 15/02 165/104.19 |
| 6,166,907 A * | 12/2000 | Chien | F28D 1/0478 165/104.33 |
| 6,498,731 B1 * | 12/2002 | Roscoe | H05K 7/1408 361/741 |
| 6,500,267 B1 * | 12/2002 | Fencl | A61L 2/10 134/1 |
| 6,591,898 B1 | 7/2003 | Chu et al. | |
| 7,403,392 B2 | 7/2008 | Attlesey et al. | |
| 7,525,207 B2 | 4/2009 | Clidaras | |
| 7,884,691 B2 | 2/2011 | Findeisen | |
| 7,983,041 B2 * | 7/2011 | Godfroy | H05K 5/06 165/104.33 |
| 8,450,381 B2 | 5/2013 | Rogers et al. | |
| 8,502,165 B2 | 8/2013 | Lee | |
| 8,854,809 B2 | 10/2014 | Neumann et al. | |
| 2003/0147214 A1 | 8/2003 | Patel et al. | |
| 2004/0173541 A1 | 9/2004 | Kurihara et al. | |
| 2004/0223300 A1 * | 11/2004 | Fink | H05K 7/20 361/690 |
| 2005/0126750 A1 * | 6/2005 | Yokozawa | F28F 3/14 165/46 |
| 2006/0185827 A1 * | 8/2006 | Huang | F28D 15/0266 165/104.25 |
| 2007/0017662 A1 * | 1/2007 | Valenzuela | F28D 15/00 165/170 |
| 2007/0034356 A1 * | 2/2007 | Kenny | F04B 17/00 165/80.4 |
| 2007/0053168 A1 * | 3/2007 | Sayir | B32B 18/00 361/718 |
| 2008/0302115 A1 * | 12/2008 | Eknes | H05K 5/068 62/183 |
| 2009/0252559 A1 * | 10/2009 | Masters | B63C 11/52 405/195.1 |
| 2009/0295167 A1 * | 12/2009 | Clidaras | F03B 13/20 290/55 |
| 2010/0254087 A1 * | 10/2010 | Godfroy | H05K 5/06 361/699 |
| 2011/0132579 A1 * | 6/2011 | Best | H05K 7/20763 165/104.31 |
| 2011/0194247 A1 | 8/2011 | Nakasaka et al. | |
| 2011/0247348 A1 | 10/2011 | Mashiko | |
| 2012/0090808 A1 | 4/2012 | Scofield | |
| 2012/0136487 A1 | 5/2012 | Lin et al. | |
| 2012/0312192 A1 * | 12/2012 | Detty | C01B 33/16 106/287.11 |
| 2013/0018491 A1 * | 1/2013 | Kelly | G01N 1/2035 700/90 |
| 2013/0032314 A1 * | 2/2013 | Baerd | H05K 7/20272 165/104.33 |
| 2013/0337201 A1 * | 12/2013 | Eyster | B63B 59/045 428/35.5 |
| 2014/0027129 A1 * | 1/2014 | Hannegan | E21B 33/085 166/387 |
| 2014/0216686 A1 | 8/2014 | Shelnutt et al. | |
| 2014/0216701 A1 | 8/2014 | Vogerl | |
| 2014/0246174 A1 | 9/2014 | Arvelo et al. | |
| 2014/0261132 A1 | 9/2014 | Zeren et al. | |
| 2014/0301036 A1 * | 10/2014 | Chainer | H05K 7/2079 361/679.47 |
| 2015/0321739 A1 | 11/2015 | Dehlsen | |

FOREIGN PATENT DOCUMENTS

| | | |
|---|---|---|
| EP | 0040651 | 12/1981 |
| EP | 2487327 | 8/2012 |
| EP | 2533621 | 12/2012 |
| EP | 2825008 | 1/2015 |
| GB | 2004704 | 4/1979 |
| WO | 2014109869 A1 | 7/2014 |

OTHER PUBLICATIONS

Office Action dated Dec. 16, 2016 cited in U.S. Appl. No. 14/272,676.

"External Fouling—The Enemy of Heat Transfer", Retrieved on: Mar. 10, 2015 Available at: http://cooneycoil.com/external-fouling-the-enemy-of-heat-transfer/.

Toma, et al., "Study on Heat Dissipation and Cooling Optimization of the Junction Box of OBSEA Seafloor Observatory", In Proceedings of IEEE/ASME Transactions on Mechatronics, Aug. 20, 2014, pp. 1-9.

"Ocean Energy to Power Google's Sea-Going Data Center", Published on: Sep. 2008 Available at: http://newenergynews.blogspot.in/2008/09/ocean-energy-to-power-googles-sea-going.html.

U.S. Appl. No. 14/319,926, James, et al., "Submerged Data Center on Ocean Floor ", filed Jun. 30, 2014.

U.S. Appl. No. 14/320,019 , James, et al., "Ocean Submerged Data Center—Pressure Equalized via Immersion Cooling Liquid ", filed Jun. 30, 2014.

U.S. Appl. No. 14/272,656, Aquantis, Inc., "Marine Subsurface Data Center Vessel".

International Search Report and Written Opinion for PCT/US2016/038840 dated Sep. 30, 2016.

International Search Report and Written Opinion for PCT/US2016/038859 dated Sep. 9, 2016.

U.S. Appl. No. 14/752,676, filed Jun. 26, 2015, Peterson et al.

"Green Data Center Blog", Available at least as early as Sep. 12, 2008. Available at <<http://www.greenm3.com/gdcblog/2008/9/12/the-under-water-data-center-response-to-risks-of-googlersquo.html>>.

Office Action, U.S. Appl. No. 14/272,656, dated Nov. 30, 2015.

Office Action dated Mar. 31, 2017 cited in U.S. Appl. No. 14/752,676.

"Second Written Opinion Issued in PCT Application No. PCT/US2016/038859", dated Jan. 30, 2017, 4 Pages.

Second Written Opinion Issued in PCT Patent Application No. PCT/US2016/0038840 dated Jun. 1, 2017.

* cited by examiner

UNDERWATER CONTAINER COOLING VIA INTEGRATED HEAT EXCHANGER

RELATED APPLICATIONS

This application is related to U.S. patent application Ser. No. 14/752,676, entitled UNDERWATER CONTAINER COOLING VIA EXTERNAL HEAT EXCHANGER, filed the same day herewith, and incorporated herein in its entirety by this reference.

BACKGROUND

Computer equipment and other electronics systems and components can generate a significant amount of heat during operation. If a sufficient amount of this heat is not removed in a timely manner, performance of the computer equipment may be compromised. In more extreme cases, inadequate heat transfer may result in damage to the computer equipment. In recognition of the need for effective heat transfer in a computing environment, some attempts have been made to improve the cooling of computer equipment through the use of various heat exchange mechanisms and systems.

For example, some systems take water from the surrounding environment and circulate the water, which may be seawater, through a heat exchanger to remove heat from the electronic equipment. The heated water is then returned to the surrounding environment and the cycle is repeated.

BRIEF SUMMARY OF SOME EXAMPLE EMBODIMENTS

At least some of the embodiments disclosed herein relate to a pressure shell with an integrated heat exchanger. In general, the pressure shell is constructed for immersion in fresh or seawater, although other fluids could additionally or alternatively be employed. It should be noted that as used herein, the term "immersion" is intended to be broadly construed and, as such, embraces arrangements where a shell, which may or may not be a pressure shell, is fully immersed at any depth below the surface of a body of water, as well as arrangements where the shell is only partly immersed, that is, only part of the shell is immersed in the water and a remaining portion of the shell is not in contact with the water, and arrangements where the shell is disposed on the surface of a body of water. More generally, the scope of the invention embraces any disposition of the shell in which one or more heat transfer surfaces of the shell are in thermal communication with a fluid in which at least part of the shell is immersed.

As well, the shells disclosed herein may or may not be pressurized, and any of the disclosed integrated heat exchangers can be implemented in connection with either a pressurized shell, which may be referred to as a pressure shell, or an unpressurized shell. The term 'shell' as used herein is intended to be broadly construed and embraces both pressurized and unpressurized shells. Finally, a 'pressurized shell' embraces, at least: a shell whose interior is at or near atmospheric pressure; a shell whose interior pressure exceeds, substantially in some embodiments, the pressure of the surrounding environment; and, a shell whose interior pressure is approximately the same as the pressure of the surrounding environment.

As will be appreciated from the foregoing, a pressurized shell whose interior is at atmospheric pressure may be required to be quite thick in its construction in order to withstand possibly large hydrostatic pressures exerted, for example, by a surrounding environment in which that pressurized shell is disposed. In contrast, a pressurized shell whose interior pressure is about the same as, or exceeds, the pressure exerted by the surrounding environment, need not be particularly thick since, in the first case, the pressure differential between the interior and the surrounding environment is relatively small. Likewise, in the case where the interior pressure of the pressurized shell exceeds the pressure exerted by the surrounding environment, the pressurized shell is similar to a balloon and can accordingly be relatively thin as compared to the case where the external pressure is greater than the internal pressure.

The pressure shell includes interior and exterior walls that are spaced apart a distance from each other, and the interior wall at least partly defines an interior space that is sized and configured to accommodate electronic equipment, such as part or all of a datacenter for example. In use, an outer surface of the exterior wall is exposed to the surrounding environment. One or more fluid passageways are disposed between and/or defined by the interior and/or exterior walls. The passageways are configured and arranged to receive a flow of coolant from the interior space so that as the coolant, transferring heat away from the electronic equipment in the interior space, circulates through the fluid passageways, heat from the coolant is transferred to the exterior wall and then from the exterior wall to the surrounding environment. Once cooled, the coolant is then directed by the fluid passageways back to the interior space to repeat the cycle. As used herein, the term 'coolant' is intended to be construed broadly and as such, embraces liquids, gases, gas/liquid combinations, and supercritical fluids. Likewise, as used herein, the term 'fluid' is intended to be construed broadly and as such, embraces liquids, gases, gas/liquid combinations, and supercritical fluids.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features can be obtained, a more particular description of various embodiments will be rendered by reference to the appended drawings. Understanding that these drawings depict only sample embodiments and are not therefore to be considered to be limiting of the scope of the invention, the embodiments will be described and explained with additional specificity and detail through the use of the accompanying drawings in which.

DETAILED DESCRIPTION OF EXAMPLE EMBODIMENTS

Conventional approaches to cooling have proved problematic for a variety of reasons. At least some of such problems relate to the structure of the various heat exchangers involved, and the disposition of the heat exchangers to their surrounding environment. For example, such heat exchangers may include tubes, surfaces, and/or other structures that are exposed to the surrounding environment, and such exposure can result in various problems, examples of which are discussed below.

One example of such a problem concerns the flow of the seawater coolant through the heat exchanger. This exposure, over time, results in biofouling, that is, the tendency of marine life to colonize exposed surfaces, thereby impeding heat transfer, and requiring time and expense in keeping the heat transfer surfaces clean.

As well, in circumstances where the cooling fluid, such as seawater for example, is taken from the surrounding environment, the internal plumbing of the cooling system and its components must be able to withstand the external pressure and corrosive effects of the cooling fluid which, in normal operation, will flow through the internal plumbing.

In light of problems and shortcomings such as those noted above, it would be useful to be able to take advantage of the heat transfer capacity of a surrounding environment, while avoiding, or at least reducing, problems such as biofouling and corrosion. It would also be useful to have a heat exchanger having a relatively large heat transfer surface, while avoiding, or at least attenuating, problems such as those noted above.

In accordance with embodiments described herein, a pressure shell with an integrated heat exchanger is provided. Fluid passageways of the integrated heat exchanger are defined by the interior and/or exterior walls and serve to direct a flow of coolant such that heat generated by electronic components disposed within an interior space of the pressure shell is transferred to a surrounding environment in which the pressure shell is immersed.

Figure 1:
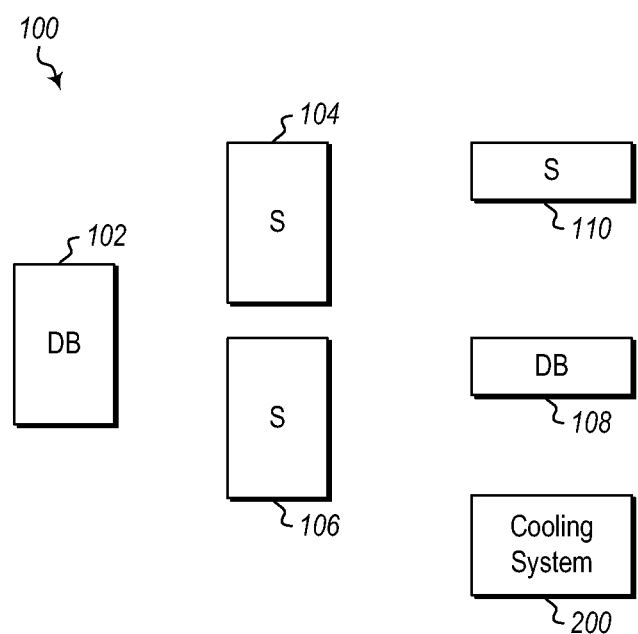
FIG. 1 discloses aspects of an example operating environment for one or more embodiments.
Figure 6:
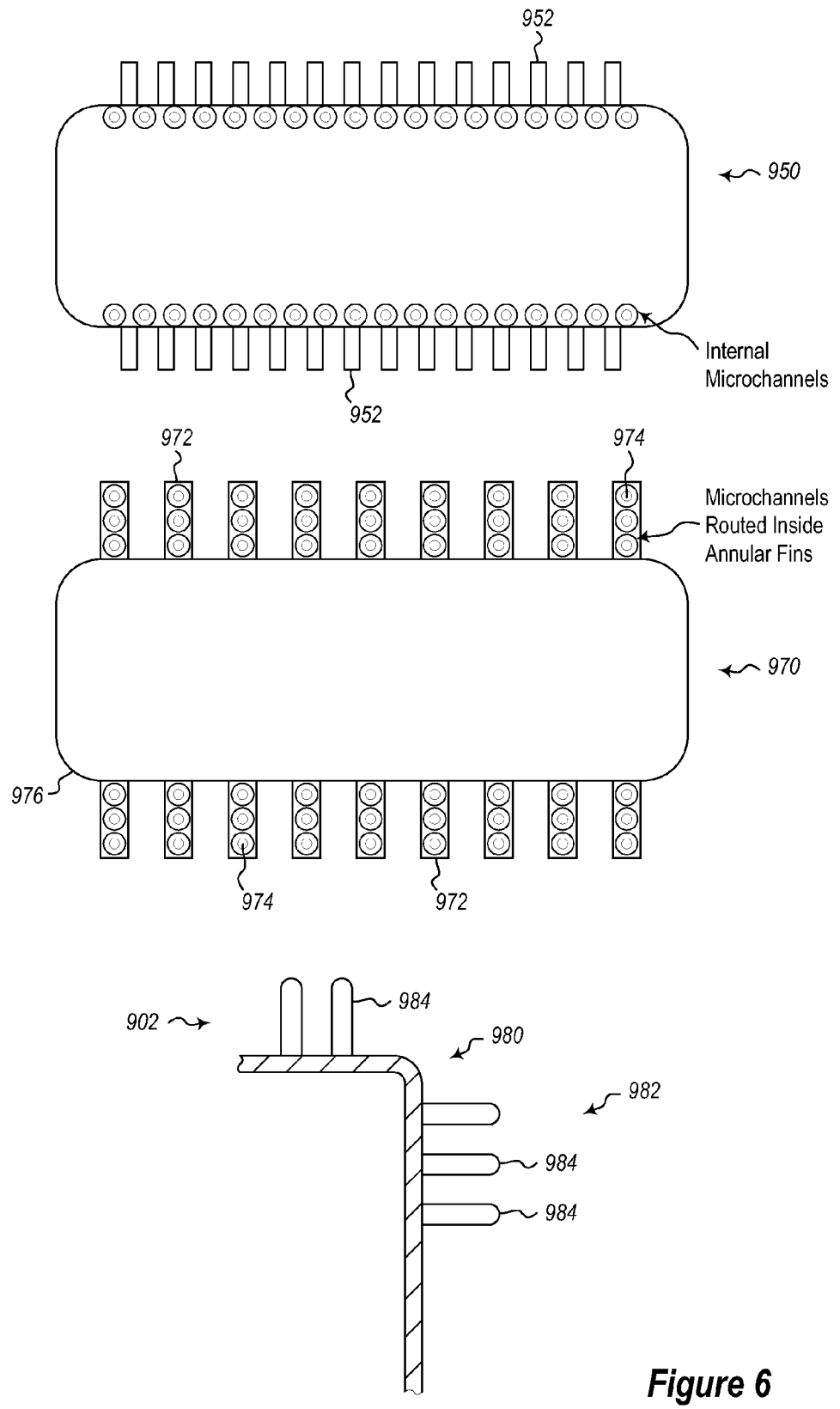
FIG. 6 discloses various alternative external configurations for a shell.
Figure 7:
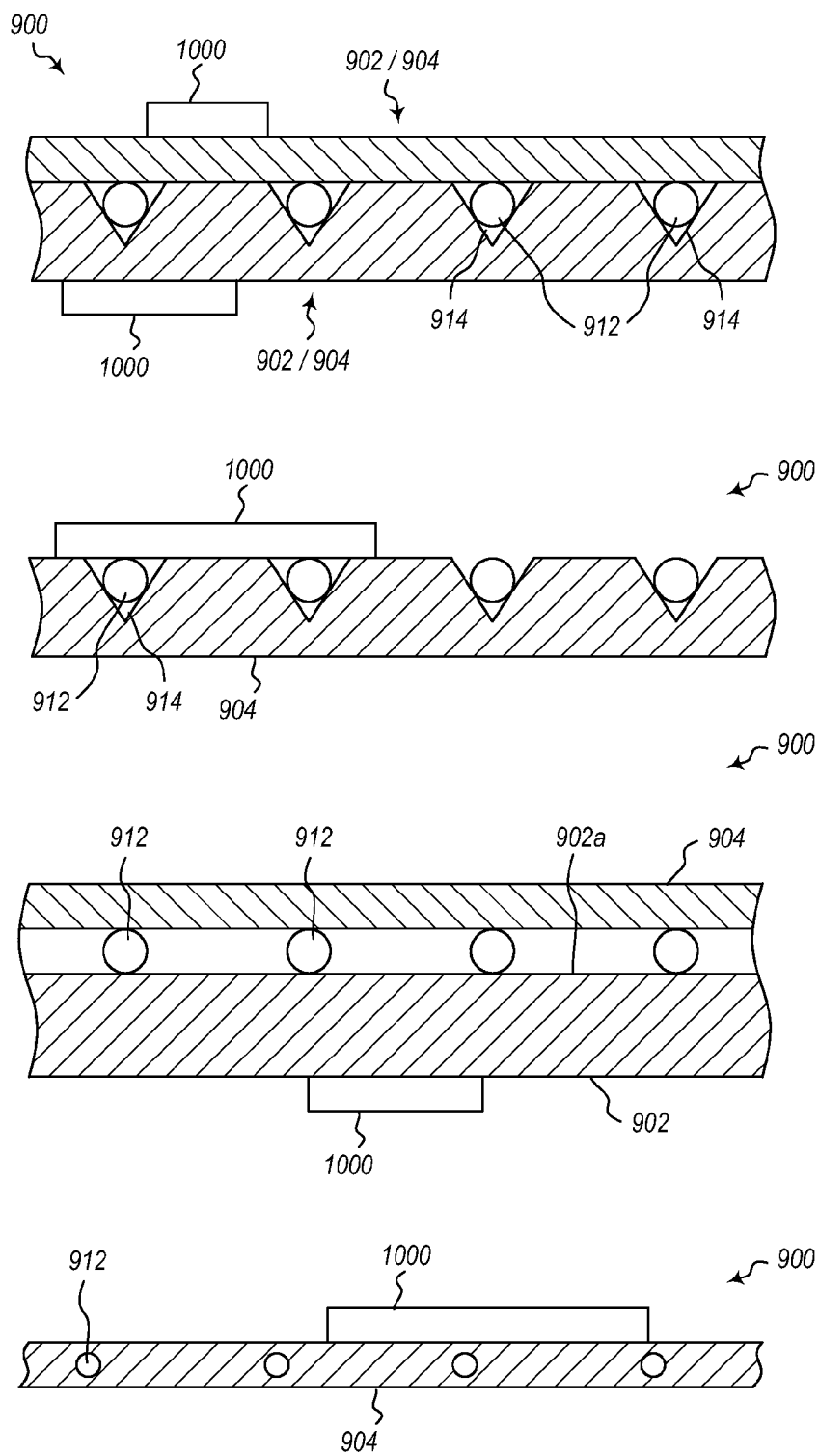
FIG. 7 discloses an example configuration where electronic equipment is mounted directly to a portion of an integrated heat exchanger.
Figure 8:
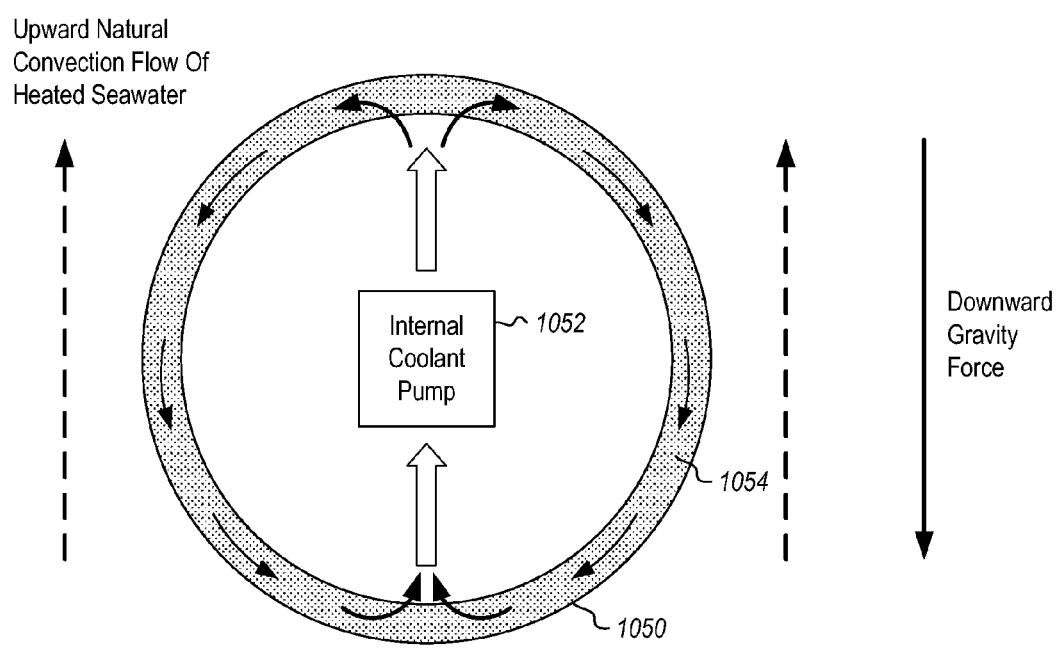
FIG. 8 discloses an example arrangement of a shell with respect to a surrounding environment.

In terms of the description of some example embodiments, some introductory discussion is first provided concerning the example operating environment disclosed in FIG. 1. Next, a description of aspects of example embodiments of a cooling system is provided with regard to the example configurations disclosed in FIGS. 2-4a. A description of an example pressure shell is presented in connection with FIG. 5a, and details of example wall configurations that form an integrated heat exchanger are addressed in the discussion of FIGS. 5b-5e. FIG. 6 concerns further aspects of example shells. FIG. 7 is directed to an arrangement in which heat generating equipment directly contacts elements of an integrated heat exchanger. FIG. 8 concerns an arrangement of a shell relative to a surrounding environment. Finally, aspects of an example method for manufacturing a shell, such as a pressure shell for example, with an integrated heat exchanger are described in connection with FIG. 9.

A. Example Operating Environments

With reference first to FIG. 1, details are provided concerning an example operating environment for at least some embodiments. One such operating environment is denoted generally at 100. In general, the disclosed embodiments can be employed in connection with any systems and equipment that require some measure of cooling in order to operate effectively and efficiently. Such systems and equipment can be, for example, mechanical, electrical, or a combination of both. In the illustrative example of FIG. 1, the operating environment is a datacenter 100, or a portion thereof. As indicated, the datacenter 100 may include, for example, one or more databases 102 and 108, servers 104, 106 and 110, and/or any other systems and equipment, such as computer network and power systems and components for example, that may be needed to implement or facilitate one or more datacenter functions.

As further indicated in FIG. 1, and discussed in more detail below in connection with FIGS. 2 and 3, the datacenter 100 may operate in connection with a cooling system 200. In general, the cooling system 200 serves to remove some, substantially all, or all, of the heat generated by the operation of the datacenter 100 systems and devices. As such, the capacity of the cooling system 200 to remove heat can be designed based upon the heat transfer requirements associated with the operation of the datacenter 100. In at least some embodiments, the cooling system 200 and datacenter 100 may be collectively implemented as a single unified system substantially, or completely, contained within a pressure vessel, as discussed in more detail below.

B. General Aspects of Example Cooling Systems

Figure 2:
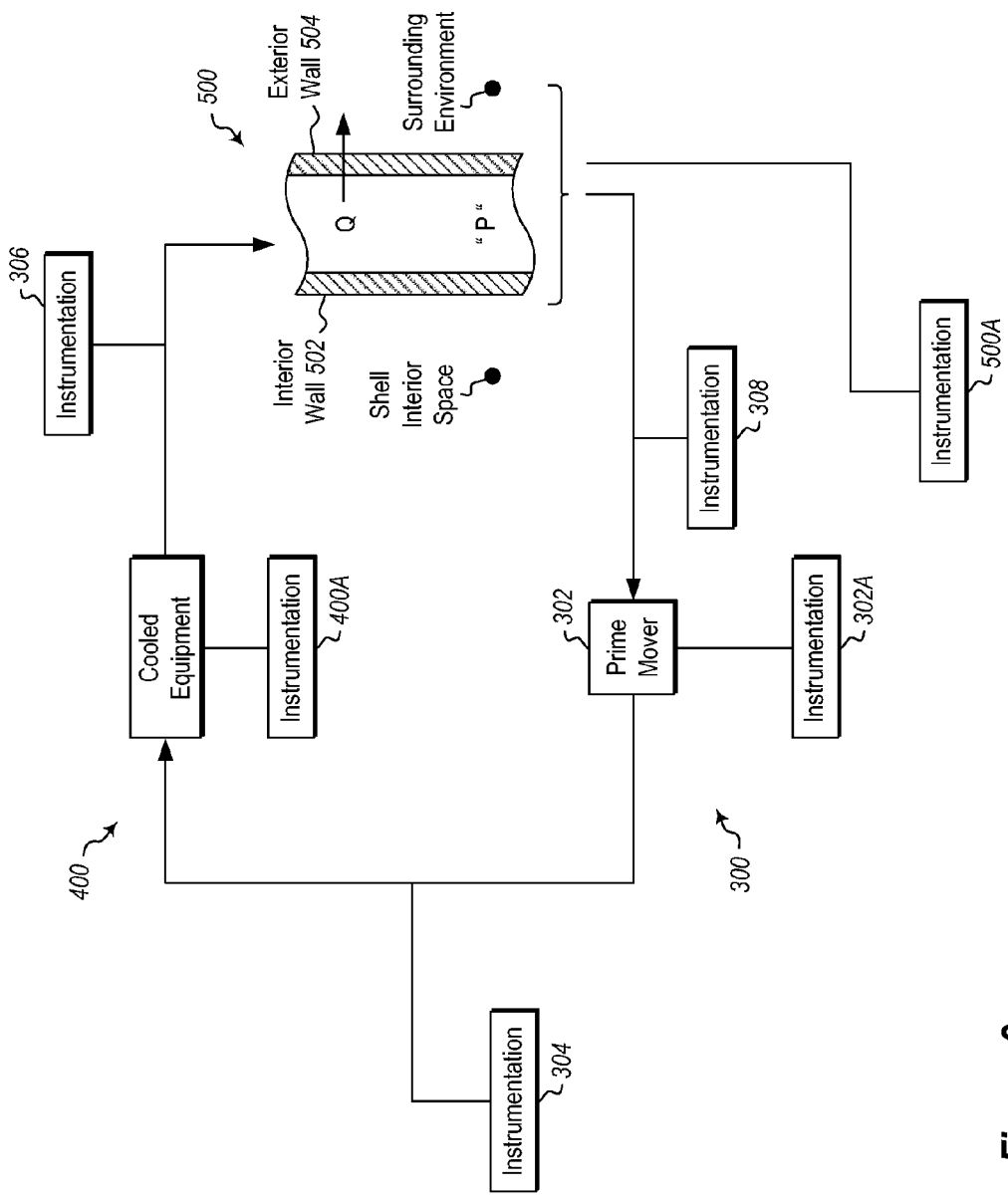
FIG. 2 is a schematic of a cooling system that includes an integrated heat exchanger of a shell.
Figure 3:
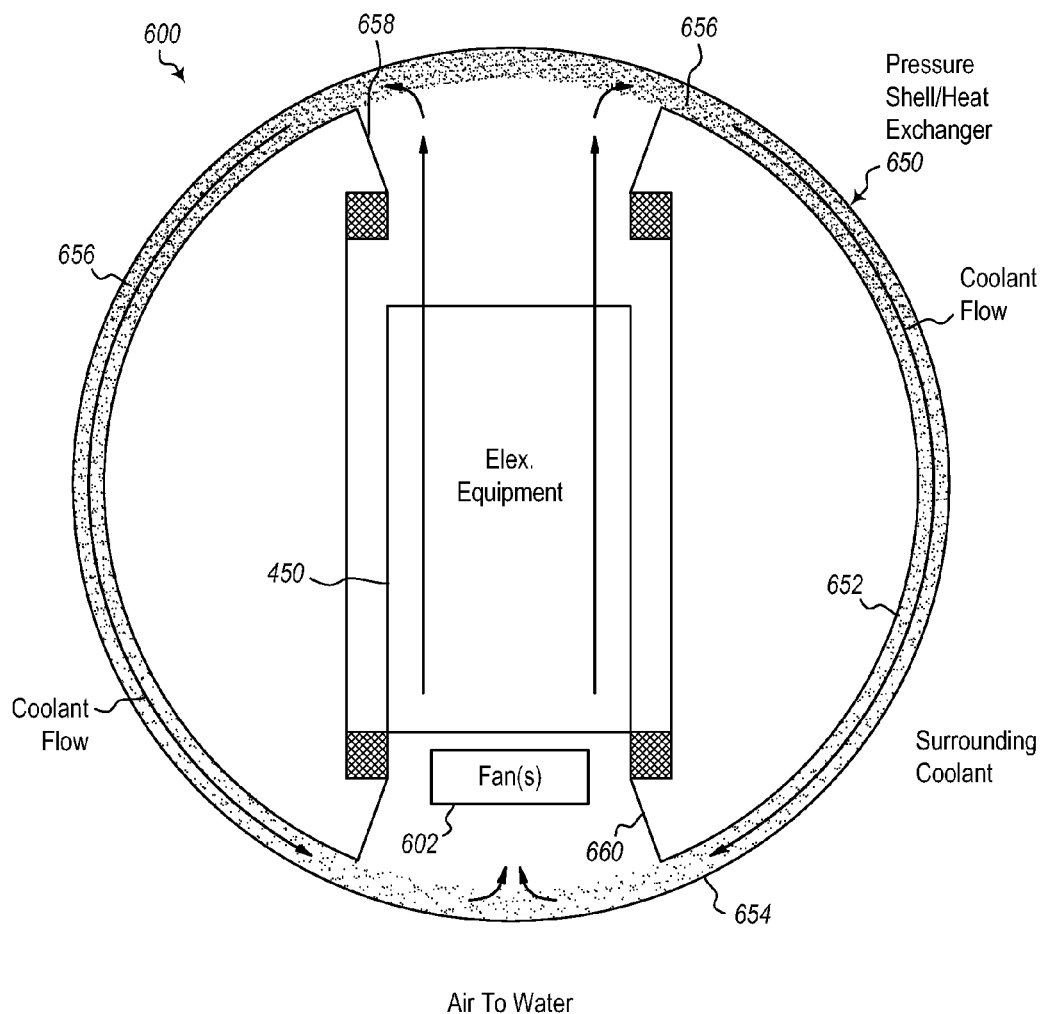
FIG. 3 discloses aspects of an example gas-fluid cooling system that includes an integrated heat exchanger of a shell.

Directing attention now to FIGS. 2 and 3, details are provided concerning basic aspects of some embodiments of a cooling system, which may be employed as the cooling system 200 disclosed in FIG. 1. The example cooling system in FIG. 2 is denoted generally at 300, and it should be noted that the considerations identified with respect to cooling system 300 apply to any of the disclosed embodiments of a cooling system.

The materials used for the components of the cooling systems disclosed herein can be any materials compatible with the coolant and the operating conditions that are expected to be encountered. Thus, some example pipe, tube, and fluid system component materials include, but are not limited to, carbon composite, titanium, aluminum, aluminum alloys, steel, copper, copper alloys, rubber and plastic.

In the illustrated example, the cooling system 300 includes a prime mover 302 that circulates a coolant to remove heat from the cooled equipment 400. As noted above, the cooled equipment 400 can comprise any equipment that generates heat during operation and, in some particular embodiments, comprises electrical/electronic equipment such as one or more components of a datacenter, and/or even the prime mover itself. In general, the prime mover 302 can be any system, device or equipment that is operable to impel a flow of coolant, such as a gas, liquid, supercritical fluid, or combinations of these. As such, the particular embodiments of a prime mover disclosed herein are presented solely by way of example and are not intended to limit the scope of the invention in any way.

In general, the liquid coolant employed in any of the disclosed cooling systems can be any suitable liquid coolant, or any combination of two or more liquid coolants. As such, the scope of the invention embraces, but is not limited to, oil, fresh water (FW), demineralized water (DW), ethylene glycol, and combinations of any of the foregoing. As some further examples, fluids which may be used in one or more of the coolant loops suitable for operating temperatures within all or a portion of the temperature range of about −10C to about 120C, with atmospheric pressures ranging from about 0.1 standard atmospheres (10.1325) kPa to about 200 standard atmospheres (20.265 MPa) or a subset include, but are not limited to, dielectric fluids, liquid mineral oil, liquid or liquid/gas or supercritical propane, liquid or liquid/gas or supercritical pentane, liquid or liquid/gas or supercritical carbon dioxide, gas or supercritical helium or nitrogen, liquid or liquid/gas or supercritical alcohols including 2,2-dimethyl-1-propanol, azeotropes and any other combinations which include one or more of the preceding items. Any or all of the foregoing example coolants can include one or more additives such as an anti-corrosive additive. Examples of coolant systems using other coolants are addressed elsewhere herein.

If the coolant is air and/or other gases, the prime mover 302 may take the form of one or more fans located upstream and/or downstream of the cooled equipment 400. On the other hand, if the coolant is liquid, or a combination of liquid and gas, the prime mover 302 may take the form of one or more pumps, which can be located upstream and/or downstream of the cooled equipment 400. In the event that the coolant is a refrigerant which can exist in gas, liquid or gas+liquid phases, the prime mover 302 can take the form of one or more compressors. More generally then, the prime mover 302 can take the form of one or more fans, pumps, or compressors. Thus, the prime mover 302 can take the form of one or more fans, pumps, or compressors. More generally, the scope of the invention extends as well to any other system(s) or device(s) operable to direct a flow of coolant.

As the circulating coolant comes into thermal communication with the cooled equipment 400, heat is transferred from the cooled equipment 400 to the coolant. As discussed in more detail in connection with FIGS. 4 and 4a, the heated coolant circulates through one or more fluid passageways "P" defined by interior and exterior walls 502 and 504, respectively, of the pressure shell 500 within which the cooling system 300 and cooled equipment 400 are disposed. Some of the heat "Q" in the coolant is then transferred through the exterior wall of the pressure shell 500 and into the surrounding environment which could be, for example, a lake, sea, reservoir, pool, ocean or other body of water, whether manmade or naturally occurring, or formed by the combined actions of humans and nature. Thus cooled, the coolant then returns to the prime mover 302 and the cycle is repeated.

As indicated in FIG. 2, various elements of the cooling system 300 and the cooled equipment 400 may include instrumentation to enable functions such as monitoring and/or control of the performance of the cooling system 300 and the temperature and operation of the cooled equipment 400. Thus, the prime mover 302 may include an instrumentation package 302a, the cooled equipment 400 may include an instrumentation package 400a, and the pressure shell 500 may include an instrumentation package 500a. Additionally, or alternatively, instrumentation packages 304, 306 and 308 can be provided at various points in the cooling system 300. Data gathered by one or more of the instrumentation packages, as well as control signals sent to one or more of the instrumentation packages, can be transmitted to a remote location by any suitable means, examples of which include optical cables, and electrical cables. Likewise, power, control and/or monitoring signals can be sent to/received from any of the cooling system 300 components and the cooled equipment 400. The same is likewise true for any of the cooling system embodiments disclosed herein.

With regard to their constituent components, any one or more of the instrumentation packages 302a, 304, 306, 308 400a, and 500a, can include, for example, any combination of alarms, flow control devices, pressure gauges, fan speed measurement devices, demineralizers and associated alarms, temperature gauges, instrumentation within components of the cooling system, such as thermocouples located inside the pipe or tubing of a cooling system, devices for measuring electrical conductivity of liquid coolants, and flow rate measurement devices for gases and liquids. Some example alarms that could be used include, but are not limited to, low/no coolant flow, high coolant flow, low coolant temperature, high coolant temperature, pressure changes such as pressure increase and pressure drop, as well as alarms relating to the specific functionality of the cooled equipment components. While not specifically illustrated, systems and equipment for monitoring and controlling the computing performance and other parameters of the cooled equipment components can also be employed.

In view of the discussion of the general arrangement disclosed in FIG. 2, it will be apparent that various cooling system configurations can be employed. Accordingly, and with continuing reference to FIG. 2, and directing attention as well to FIG. 2a, further details concerning some additional example configurations are set forth below.

Figure 2A:
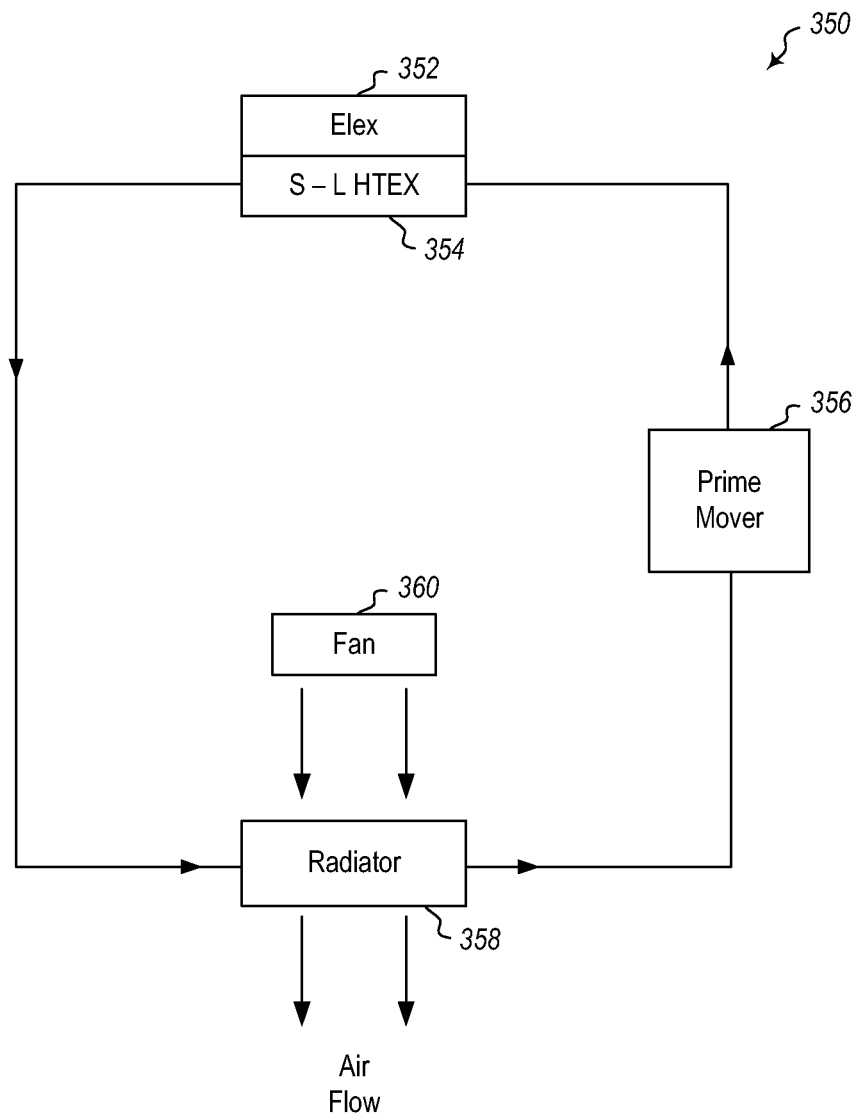
FIG. 2a is a schematic that discloses aspects of an alternative cooling system configuration that includes a solid-liquid heat exchanger.

In the example of FIG. 2a, a cooling system configuration is disclosed that includes a solid-liquid heat exchanger. It should be noted that instrumentation and other components such as disclosed in FIG. 2 and/or discussed elsewhere herein (see, e.g., FIG. 4) can be employed in the example of FIG. 2a, but have been omitted from FIG. 2a in the interest of clarity.

As indicated, a cooling system 350 serves cooled equipment 352 which can include high power electronic components such as central processing units (CPU) and/or other types of components and chips. It should be noted that as used herein, the relative power of a component refers to the heat generating ability of that component. In the embodiment of FIG. 2a, a solid-liquid HTEX 354 is provided that is in thermal communication with cooled equipment 352, such as semiconductor chips for example. This HTEX 354 may be similar to a gas-to-liquid heat exchanger except that the HTEX 354 has one or more surfaces configured and arranged to provide direct thermal communication with, and thermal conduction, from the cooled equipment 352 and/or other components to the liquid coolant circulating through the HTEX 354. This thermal communication can be achieved in a variety of ways, such as through the use of surfaces that are very smooth and/or include any other characteristics which facilitate heat transfer.

The coolant is circulated through the HTEX 354 by a prime mover 356, such as one or more pumps for example. The heated coolant leaving the HTEX 354 passes through a secondary HTEX 358. The HTEX 358 can be any suitable type of heat exchanger. In some embodiments at least, the HTEX 358 is a radiator, which may be similar in structure and operation to a car or truck radiator. In particular, the HTEX 358 in such embodiments may include a series of tubes that are in fluid communication with the HTEX 354, and are also in thermal communication with a plurality of extended surfaces, such as fins for example. One result of this configuration is that heated coolant circulating through the tubes of the HTEX 358 transfers heat to the fins, which may have a relatively large surface area to facilitate heat dissipation. The fins, in turn, can be cooled by a flow of a coolant, such as air and/or other gas(es) for example, provided by a prime mover 360, such as one or more fans. The coolant, thus cooled by the HTEX 358, then returns to the HTEX 354 to repeat the cycle.

It should be noted that cooling systems and components such as those disclosed in FIG. 2a can be combined with other cooling systems, including the particular examples noted below in FIGS. 3, 4 and 4a for example, to provide cooling for systems that include both high power electronics, and relatively lower power electronics. Thus, a pressure shell can include at least two different cooling systems, one of which may be embodiments of a cooling system such as disclosed in FIG. 2a, and another of which may be a cooling system such as the various embodiments disclosed in FIGS. 3, 4 and 4a-4d. In embodiments where, as noted above, two different cooling systems are employed, the different cooling systems may be isolated from, and operate independently of, each other. Some example embodiments of arrangements that include multiple cooling systems are disclosed elsewhere herein.

C. Aspects of An Example Gas-Fluid Cooling System

Directing attention now to FIG. 3, and with the discussion of FIGS. 2 and 2a in view, details are provided concerning an example cooling system, denoted generally at 600, that can be used, for example, to provide cooling for electronic equipment. In the illustrated embodiment, the cooling system 600 is a gas-fluid cooling system that uses a gas, or gases, as the primary coolant. In general, the gas can be any gas, or combination of gases, that can be used to remove heat from electronic equipment 450. As well, the fluid component of the gas-fluid cooling system can be any fluid, or combination of fluids, in which a pressure shell, such as those disclosed herein, can be partially or completely immersed, and which can effect heat transfer from the gas. As such, the fluid may be freshwater or seawater, for example.

In the example of FIG. 3, the gas-fluid cooling system 600 includes one or more fans 602 which can be located upstream and/or downstream and/or in any other location relative to the electronic equipment 450 so as to effect a flow of gas, such as air or other gas(es) in the atmosphere of the pressure shell 650 for example, with respect to the electronic equipment 450, thereby cooling the electronic equipment 450. As such, the fans 602 can push and/or pull a flow of gas into thermal communication with the electronic equipment 450. The fans 602 can be any type of fan, although some embodiments may employ one or more vaneaxial fans, tube axial fans, or any fan that includes a reverse blade impeller, for example. In some embodiments, the fans 602 can be connected to ductwork (such as 660 noted below) that directs the flow of gas to the electronic equipment 450 and/or ductwork (such as 658 noted below) can be provided downstream of the electronic equipment 450 so as to direct the heated gas into fluid passageways, discussed below, of the pressure shell 650. In at least some embodiments, the ductwork by way of which the coolant is supplied to/from the electronic equipment 450 is in the form of a closed system that is substantially, or completely, sealed off from the interior space of the pressure shell 650. Correspondingly, the ductwork may be thermally insulated so that little or no heat transfer occurs between the coolant and the interior space of the pressure shell 650.

As further indicated in FIG. 3, the pressure shell 650 forms an element of the gas-fluid cooling system 600. The pressure shell 650 can have any suitable shape, examples of which include, but are not limited to spherical, and cylindrical with domed end caps. In the illustrated example, a cross-section of a cylindrical shell is shown and the pressure shell 650 includes a wall structure that has an interior wall 652 and an exterior wall 654. Disposed between the interior wall 652 and exterior wall 654 are one or more fluid passageways 656. As discussed elsewhere herein, the fluid passageways 656 may be defined in whole or in part by the interior wall 652 and/or the exterior wall 654. That is, the pressure shell 650 includes an integrated heat exchanger that comprises the fluid passageways 656 defined by the interior wall 652 and exterior wall 654. Further details concerning specific configurations of fluid passageways, such as fluid passageways 656 for example, are provided below in the discussion of FIGS. 5a-5e.

With continuing reference to FIG. 3, the fluid passageways 656 can communicate with one or more inlet connections 658 and one or more outlet connections 660, such that gas pressurized by the fans 602 can be directed to the fluid passageways 656 by way of the inlet connections 658. The pressurized gas then passes through the fluid passageways 656 and returns to the fans 602 by way of the outlet connections 660, as indicated in FIG. 3. The inlet connections 658 and outlet connections 660 can be defined at least in part by the interior wall 652 of the pressure shell 650.

To briefly summarize the operation of the embodiment of FIG. 3 then, a flow of gas in the interior of the pressure shell 650 is directed by one or more fans 602 into thermal communication with the electronic equipment 450 and thereby removes heat from the electronic equipment 450. The heated gas then enters the fluid passageways 656 by way of the inlet connections 658 and contacts the exterior wall 654, which is at a lower temperature than the heated gas by virtue of the contact between the exterior wall 654 and the surrounding coolant. This temperature differential results in a transfer of heat from the gas to the exterior wall 654, and then to the surrounding coolant. The cooled gas then exits the fluid passageways 656 by way of the outlet connections 660 and returns to the fans 602 to repeat the cycle.

As can be appreciated from the foregoing discussion, one aspect of this example embodiment is that none of the surrounding coolant, that is, from the environment in which the pressure shell 650 is immersed, ever enters the pressure shell 650. Instead, the gas coolant is simply recirculated in the interior space defined by the pressure shell 650. Thus, problems associated with conditions such as biofouling and corrosion may at least be attenuated in such an embodiment. As well, the need for penetrations of the pressure shell 650 is reduced since there is no fluid communication between the gas-fluid cooling system 600 and the surrounding coolant. It should also be apparent from the foregoing discussion that the cooling system embodiments disclosed herein may operate in connection with any one or more of the various modes of heat transfer, namely, convection, conduction, and radiation.

It will be appreciated that variations of the example configuration of FIG. 3 can be implemented. In one particular example, and with reference now to FIG. 3a, the arrangement of FIG. 3 can include one or more additional cooling systems, one example of which is discussed above in connection with FIG. 2a. In the following discussion of FIG. 3a, it should be noted that in the interest of clarity, not all the components indicated in FIG. 2a are illustrated in FIG. 3a, although it should be understood that the entire system of FIG. 2a and/or alternative systems and components can be included in the arrangement of FIG. 3a.

Figure 3A:
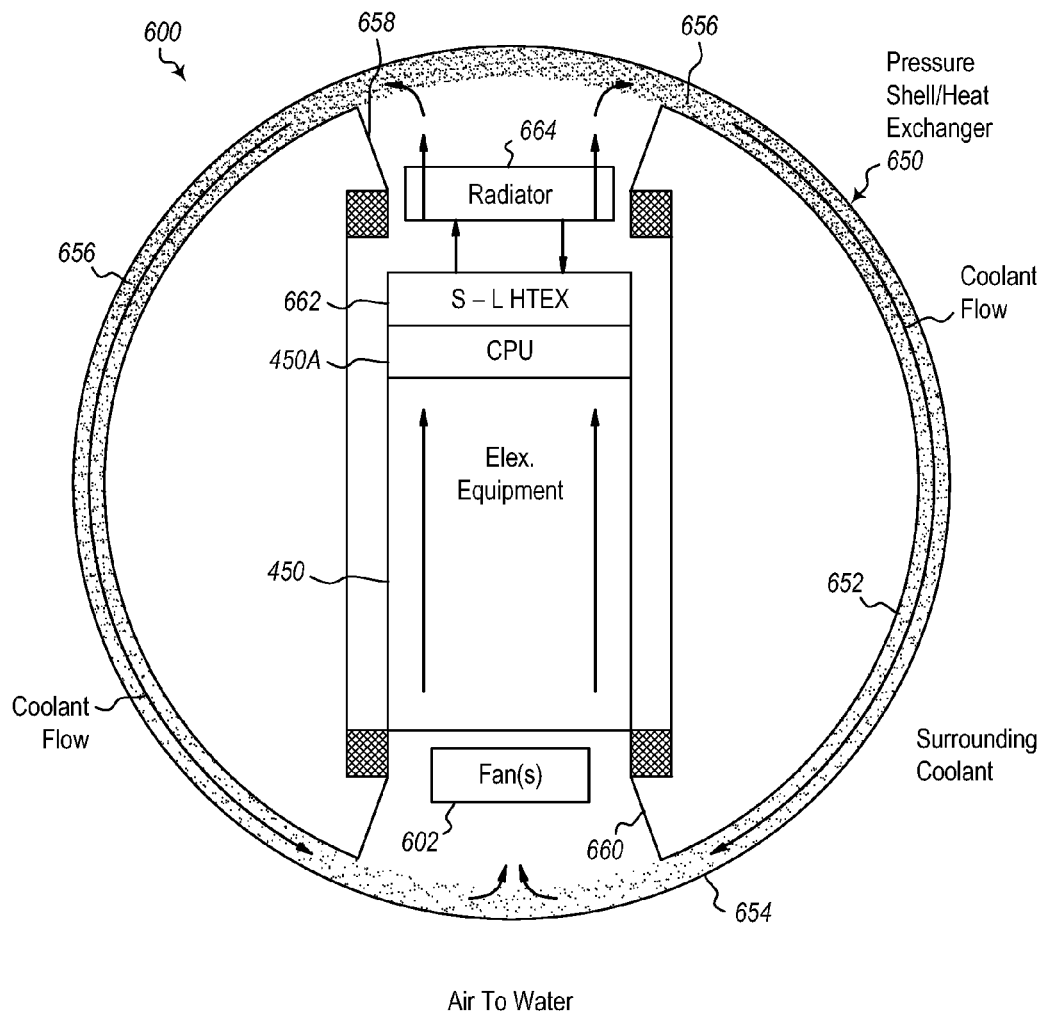
FIG. 3a discloses aspects of an arrangement that includes multiple cooling systems.

In the arrangement of FIG. 3a, provision is made for a first cooling system that serves relatively low power electronic components, as well as for a second cooling system that serves relatively high power electronic components. As shown, the second cooling system includes a solid-liquid HTEX 662 that is in thermal communication with cooled equipment 450A, such as high power electronic components (and, also cooled equipment 352 in FIG. 2a) like one or more CPUs for example. In addition to the HTEX 662, another HTEX, such as radiator 664 for example, can be provided that, in general, serves to remove heat from coolant received by the radiator 664 from the HTEX 662, as shown in the example configuration of FIG. 2a.

In operation, coolant circulating through the HTEX 662 removes heat from the cooled equipment 450A and is directed from the HTEX 662 to the radiator 664. As indicated in FIG. 3a, the air or other gas circulated by the fans 602 comes into thermal communication with fins or other heat transfer surfaces of the radiator 664 and removes heat from the fins that has been transferred to the fins by the liquid coolant that is circulating through the radiator 664. As such, the radiator 664 is the heat source to which the air or other gas is directed. The flow of gas or other coolant from prime movers such as the fans 602 also cools the electronic equipment 450, which may be low power electronic equipment. The heated gas then enters the fluid passageways 656 and is cooled as discussed in connection with FIG. 3. This modification of the arrangement disclosed in FIG. 3 to include HTEX 662, the radiator 664 and associated cooling system components, may be especially well suited for use in cooling relatively high power electronics, such as one or more CPUs for example.

In connection with the embodiment of FIG. 3a, it should be noted that, more generally, any fluid can be used as a coolant for the electronic equipment 450 and/or cooled equipment 450a, and such fluids include gases, liquids, supercritical fluids, and any combinations of these. Similarly, the scope of this embodiment is not limited solely to fans 602 but embraces other prime movers as well, such as pumps, and compressors, for example.

D. Aspects of An Example Gas-Fluid-Fluid Cooling System

Figure 4:
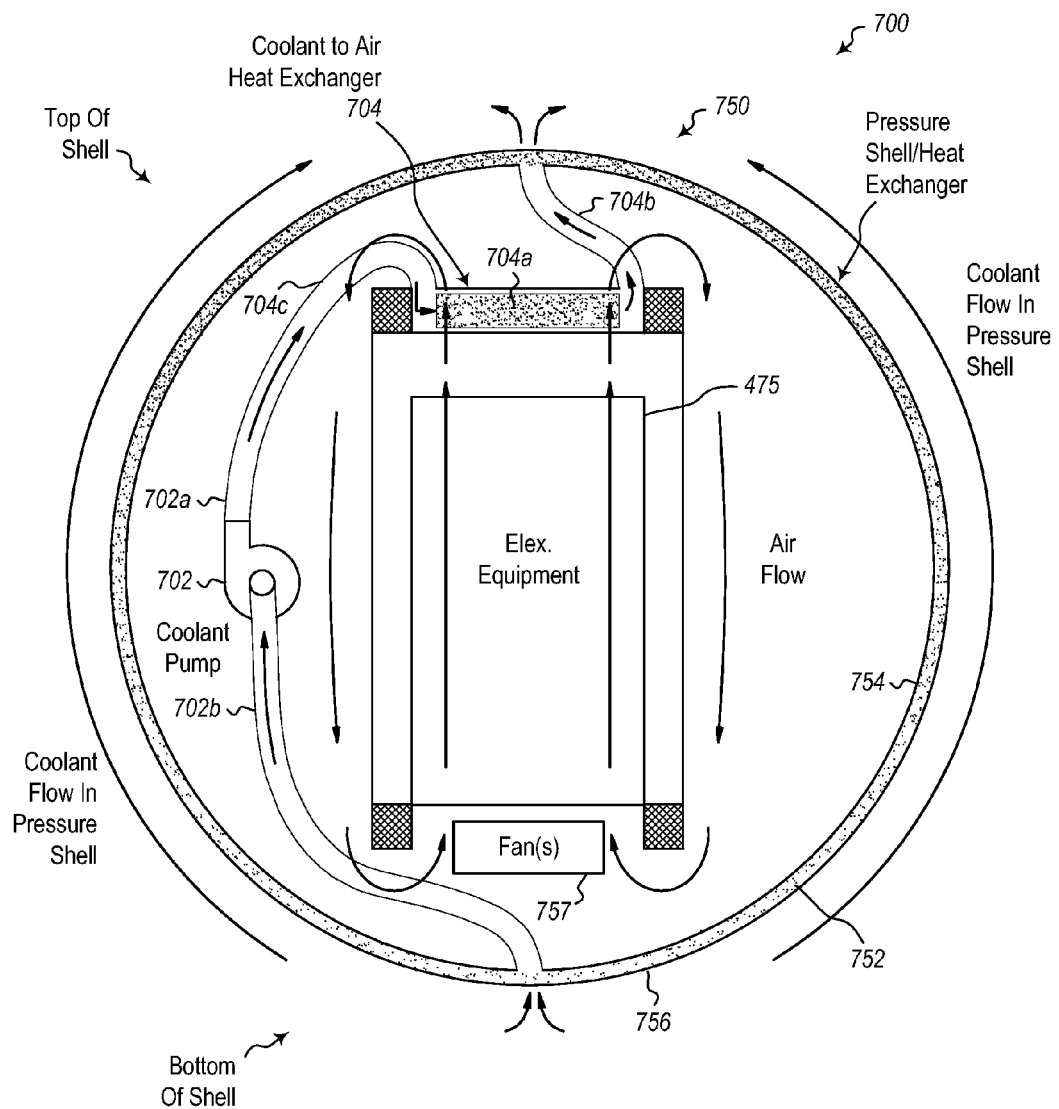
FIG. 4 discloses aspects of an example gas-fluid-fluid cooling system that includes an integrated heat exchanger of a shell.

Directing attention now to FIG. 4, details are provided concerning an example cooling system, denoted generally at 700, that can be used, for example, to provide cooling for electronic equipment. Except as noted below, the cooling system 700 can be similar, or identical, to the cooling system 600.

One useful aspect of this embodiment and other like embodiments is that inasmuch as a liquid coolant rather than a gas coolant is circulated through the pressure shell, as discussed below, relatively less heat transfer surface area is required than would be the case where the coolant is a gas, such as air. As well, because a liquid coolant is generally more efficient at transferring heat than a gas coolant, the heat flux associated with a liquid coolant is relatively higher than a heat flux that would be associated with a gas coolant. Consequently, it is easier to cool the liquid coolant during the timeframe that the liquid coolant is passing through the fluid passageways of the pressure shell.

In the illustrated embodiment, the cooling system 700 is a two-stage gas-fluid-fluid cooling system that uses a gas, or gases, as the primary coolant, and a circulating fluid as the secondary coolant. In general, the gas, which in some embodiments is simply the atmospheric gas(es) provided in the pressure shell 750, can be any gas, or combination of gases, that can be used to remove heat from the cooled equipment 475. The secondary coolant can be any suitable liquid coolant, examples of which include, but are not limited to, oil, fresh water (FW), demineralized water (DW), ethylene glycol, and combinations of any of the foregoing. Any or all of the foregoing example coolants can include one or more additives such as an anti-corrosive additive.

As indicated in FIG. 4, the cooling system 700 can include a coolant pump 702 that is in fluid communication with a gas-liquid heat exchanger (HTEX) 704, and that is also in fluid communication with one or more fluid passageways 752 defined by the interior wall 754 and exterior wall 756 of the pressure shell 750. In some embodiments, the coolant pump 702 is a centrifugal pump, but that is not required. Note that while the coolant pump 702 is arranged to discharge coolant to the HTEX 704, the arrangement of the coolant pump 702 can be reversed in other embodiments. That is, the coolant pump 702 could alternatively be arranged to take suction from the HTEX 704.

The HTEX 704 can be any suitable heat exchanger and, in one example embodiment, can have generally the same basic structure and mode of operation as a radiator such as may be employed in a motor vehicle. In particular, the HTEX 704 may be a gas-to-coolant heat exchanger having a tube-and-fin configuration that includes one or more fluid passageways 704a that communicate with a fluid outlet 704b that, in turn, is in fluid communication with the fluid passageways 752. A plate-and-fin configuration could alternatively be employed for the HTEX 704. The HTEX 704 may also include a fluid inlet 704c in fluid connection with the fluid passageways 752 and with a discharge side 702a of the coolant pump 702. The coolant pump 702 takes suction from the fluid passageways 752 by way of a suction side 702b. While not specifically illustrated in FIG. 4, it will be appreciated that the HTEX 704 may include a plurality of extended surfaces, such as fins for example, that are in thermal communication with the fluid passageways 752. In operation, heated gas from the cooled equipment 475 is directed by one or more fans 757 into contact with heat transfer surfaces of the HTEX 704, thereby transferring heat to the secondary coolant circulating in the HTEX 704. The heated secondary coolant then flows through the fluid passageways 752 where heat from the secondary coolant is transferred to the exterior wall 756 of the pressure shell 750 and then to the surrounding environment.

It should be noted that while not specifically shown in FIG. 4, one or more fans 757 can be located not only at the lower, relatively cooler, end of the cooled equipment 475 (as shown), but also at the upper, relatively hotter, end of the cooled equipment 475. In yet other embodiments, one or more fans 757 are located only at the upper, relatively hotter, end of the cooled equipment 475, and fans at the lower end of the cooled equipment 475 are omitted.

The materials used for the components of the cooling system 700 can be any materials compatible with the coolant and the operating conditions that are expected to be encountered. Thus, some example pipe, tube, and fluid system component materials include, but are not limited to, aluminum, aluminum alloys, steel, copper, copper alloys, rubber and plastic.

Figure 4A:
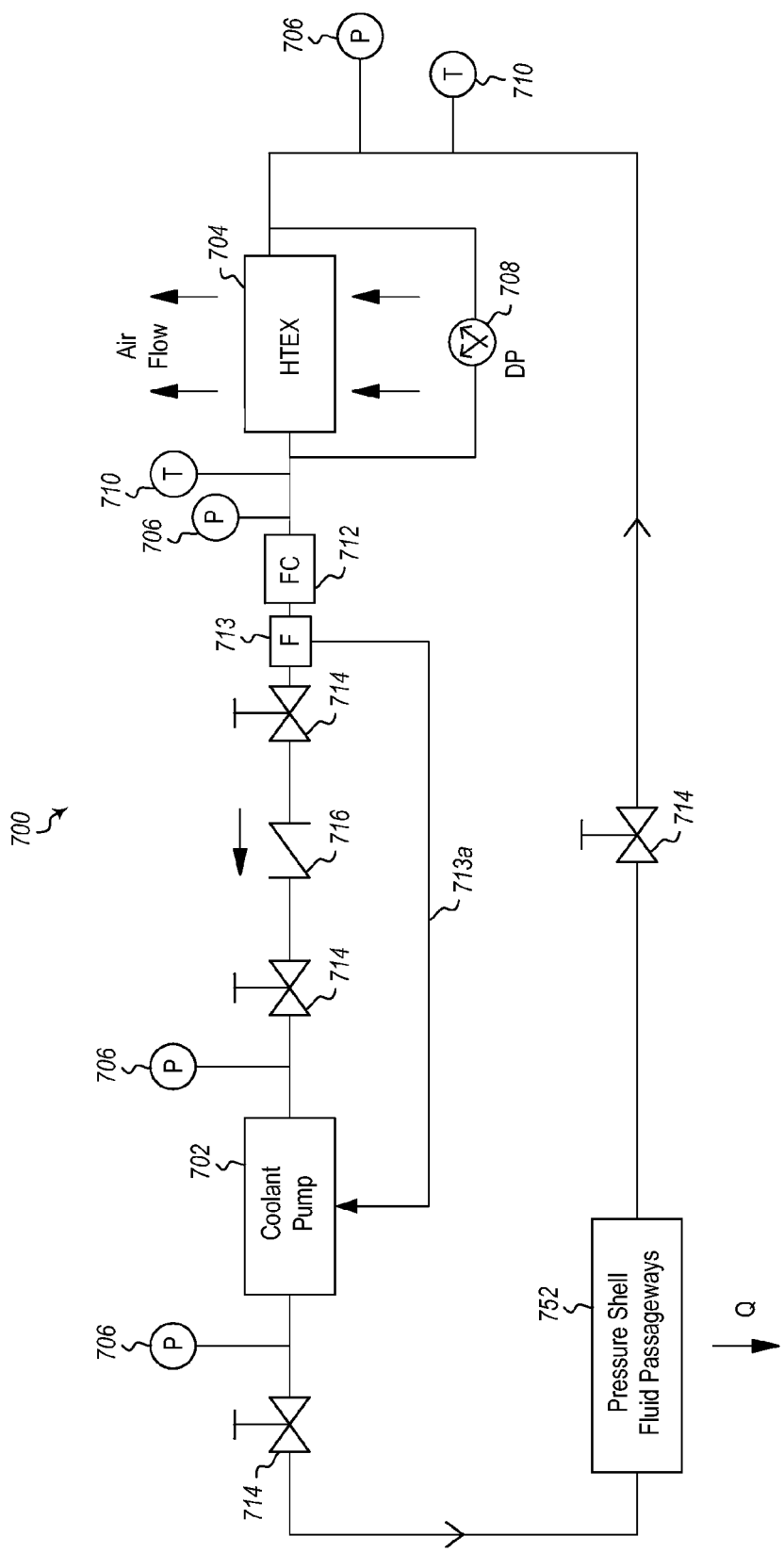
FIG. 4a is a schematic representation of a cooling system such as the cooling system of FIG. 4.

With continued reference to FIG. 4, and directing attention now to FIG. 4a, a schematic illustration of an example cooling system that includes the elements of cooling system 700 is discussed. In addition to the components discussed in connection with FIG. 4, the cooling system 700 may also include, for example, instrumentation such as pressure gauges 706 upstream and downstream of the coolant pump 702, and upstream and downstream of the HTEX 704. Yet other instrumentation can monitor coolant pump 702 speed. Of course, more or fewer pressure gauges can be used in the foregoing and/or alternative locations throughout the cooling system 700. In some embodiments, a differential pressure (DP) gauge 708 can be used in connection with the HTEX 704 to enable a user to determine, by the magnitude of the pressure differential, or pressure drop, across the HTEX 704, when the HTEX 704 should be cleaned, checked for leaks, or replaced. The cooling system 700 can further include instrumentation such as temperature gauges 710 upstream and downstream of the HTEX 704 and/or in any other suitable locations in the cooling system 700.

In addition to instrumentation, the cooling system 700 can include various other fluid system components such as, for example, a flow control device 712, which can be located downstream of the HTEX 704. In general, the flow control device 712 may help to ensure that a coolant flow rate through the HTEX 704 remains within a desired range. The flow control device 712 is not required however, and can be omitted. In some embodiments, a flow meter 713, such as a venturi for example, can be used to indicate the flow rate out of the HTEX 704. If desired, a feedback connection 713a can be provided that provides the flow rate information as an input to the coolant pump 702 controller. Other components of the cooling system 700 can include one or more isolation valves 714, and one or more backflow preventers such as check valves 716.

As in the case of other disclosed embodiments, it will be appreciated that various modifications can be made to the arrangements indicated in FIGS. 4 and 4a. Accordingly, attention is directed now to the embodiment of FIG. 4b which, similar to the embodiment of FIG. 3a, may include multiple cooling systems, each of which is concerned with particular equipment that is to be cooled.

Figure 4B:
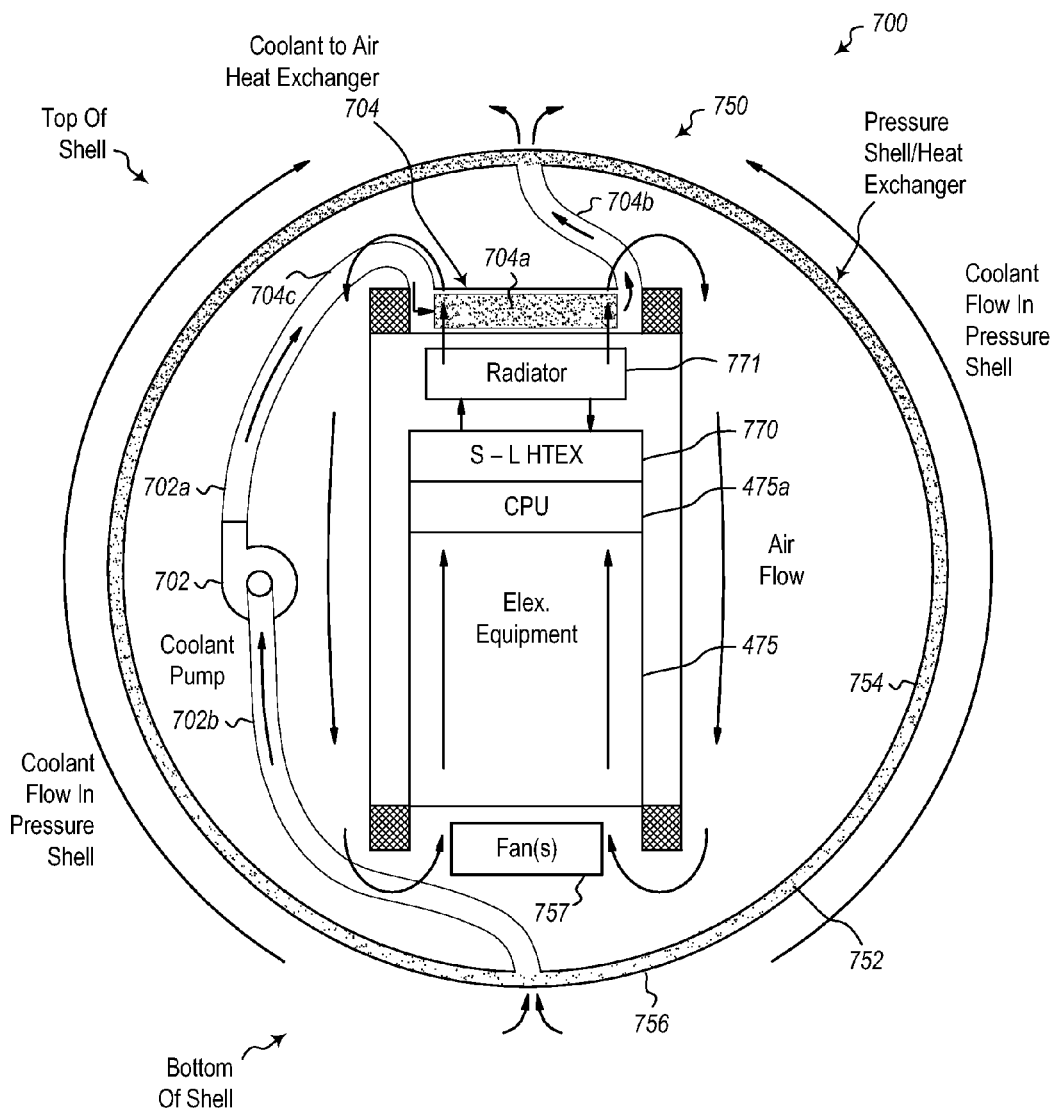
FIG. 4b discloses aspects of an arrangement with multiple cooling systems, one of which includes a radiator.

In FIG. 4b, and with continuing attention to FIG. 4, the arrangement of FIG. 4 can include one or more additional cooling systems, one example of which is discussed above in connection with FIG. 2a. In the following discussion of FIG. 4b, it should be noted that in the interest of clarity, not all the components indicated in FIG. 2a are illustrated in FIG. 4b, although it should be understood that the entire system of FIG. 2a and/or alternative systems and components can be included in the arrangement of FIG. 4b.

In the arrangement of FIG. 4b, provision is made for a first cooling system that serves relatively low power electronic components, as well as for a second cooling system that serves relatively high power electronic components. As shown, the second cooling system includes a solid-liquid HTEX 770 that is in thermal communication with cooled equipment 475a, such as high power electronic components (and, also cooled equipment 352 in FIG. 2a) like one or more CPUs for example. In addition to the HTEX 770, another HTEX, such as radiator 771 for example, can be provided that, in general, serves to remove heat from coolant received by the radiator 771 from the HTEX 770, as shown in the example configuration of FIG. 2a.

In operation, coolant circulating through the HTEX 770 removes heat from the cooled equipment 475a and is directed from the HTEX 770 to the radiator 771. As indicated in FIG. 4b, the air or other gas circulated by the fans 757 comes into thermal communication with fins or other heat transfer surfaces of the radiator 771 and removes heat from the fins that has been transferred to the fins by the liquid coolant that is circulating through the radiator 771. Additionally, or alternatively, heat from the radiator 771 is transmitted by radiation through the atmosphere of the pressure shell to the HTEX 704, where the radiated heat is then transferred to the coolant circulating through the HTEX 704. In such an arrangement, it can be desirable to locate the radiator 771 relatively close to the HTEX 704 so as to enhance radiative heat transfer from the radiator 771 to the HTEX 704. The flow of gas or other coolant from prime movers such as the fans 757 also cools the cooled equipment 475, which may be low power electronic equipment, and cools the HTEX 704.

This modification of the arrangement disclosed in FIG. 4 to include HTEX 770, the radiator 771 and associated cooling system components, may be especially well suited for use in cooling relatively high power electronics, such as one or more CPUs for example. In connection with the embodiment of FIG. 4b, it should be noted that, more generally, any fluid can be used as a coolant for the cooled equipment 475 and/or 475a, and such fluids include gases, liquids, supercritical fluids, and any combinations of these. Similarly, the scope of this embodiment is not limited solely to fans 757 but embraces other prime movers as well, such as pumps, and compressors, for example.

Figure 4C:
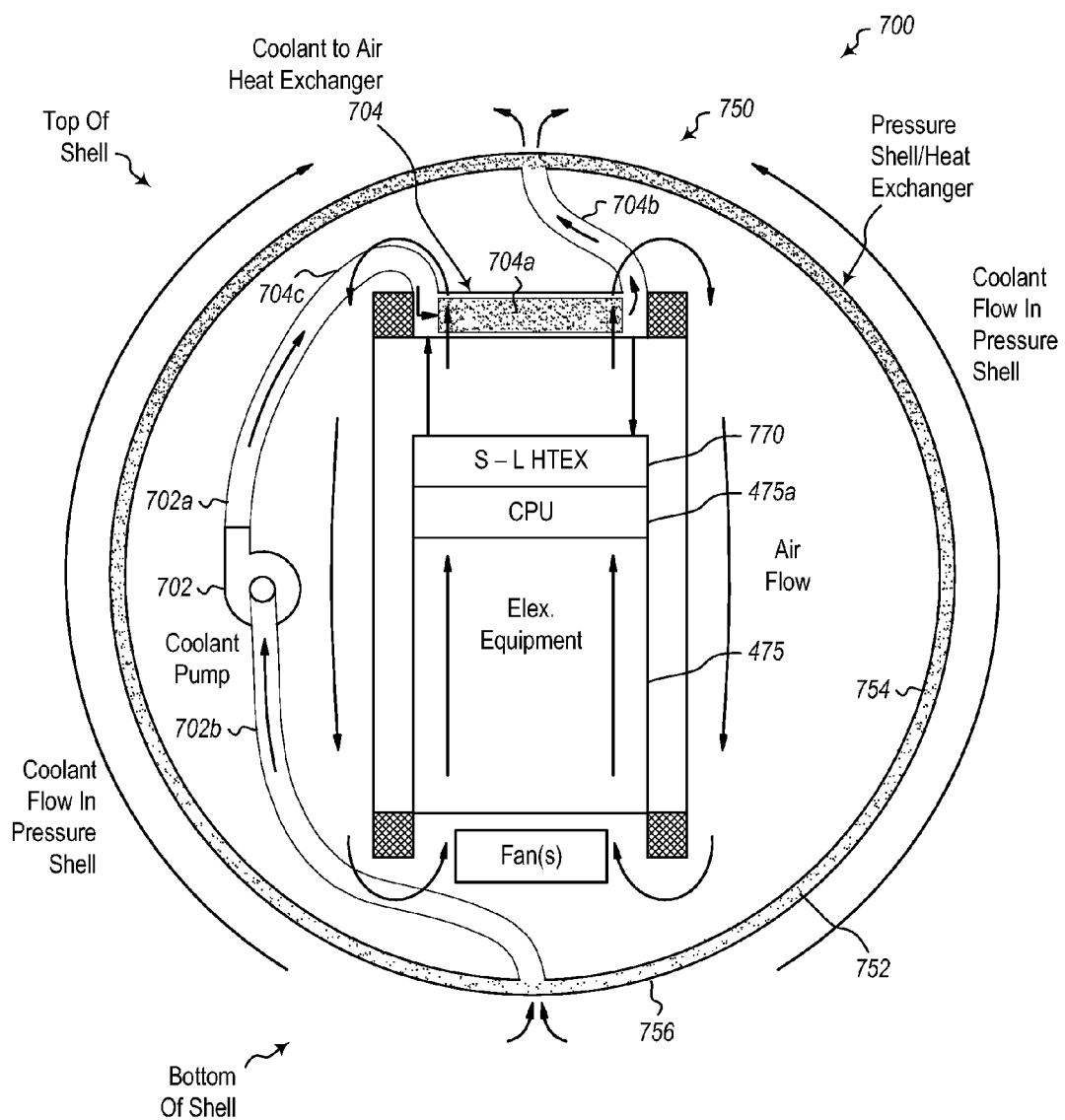
FIG. 4c discloses aspects of an arrangement in which multiple heat exchangers are arranged in parallel.

In another variation of the arrangements of FIGS. 4 and 4a, and directing attention now to FIG. 4c, an arrangement is disclosed that does not employ a radiator such as is used in the embodiment of FIG. 4b. Similar to the arrangement in FIG. 4b, a solid-liquid HTEX 770 may be provided that is in thermal communication with cooled equipment 475a, such as one or more CPUs for example. As in the case of the other solid-liquid HTEX devices disclosed herein, the solid-liquid HTEX 770 may be an integrated element of the cooled equipment 475a. In the arrangement of FIG. 4c however, HTEX 770 is connected to the shell cooling system in parallel with HTEX 704. In one variation of the FIG. 4c arrangement, the HTEX 770 can be connected to the shell cooling system in series with HTEX 704 such that the HTEX 770 is either upstream or downstream of the HTEX 704.

Figure 4D:
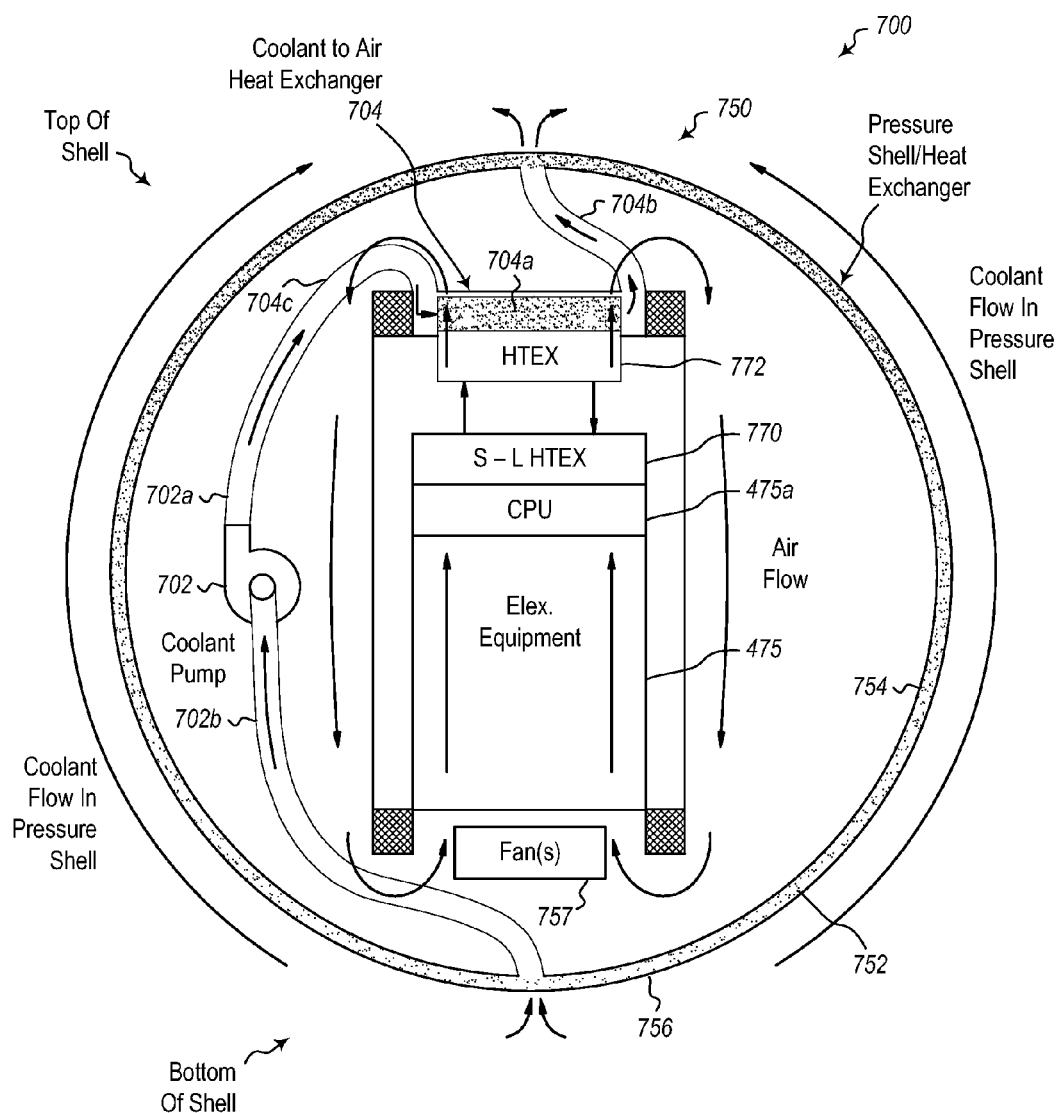
FIG. 4d discloses aspects of a cooling system that includes multiple integrated heat exchangers.

In another variation of the arrangements of FIGS. 4 and 4a, and directing attention now to FIG. 4d, a solid-liquid HTEX 770 may be provided that is in thermal communication with cooled equipment 475a, such as one or more CPUs for example. As in the case of the other solid-liquid HTEX devices disclosed herein, the solid-liquid HTEX 770 may be an integrated element of the cooled equipment 475a.

As well, the HTEX 770 is in fluid communication with a liquid-liquid HTEX 772. In some embodiments, the HTEX 772 is integrated together with the HTEX 704, which may be a radiator, although that is not required. Further, the HTEX 772 could include extended surfaces such as fins to aid in heat transfer, although such surfaces are not required. When so integrated together, the HTEX 772 and HTEX 704 collectively form a heat exchanger with two separate liquid channels and one air/gas channel. The integrated heat exchanger may include extended surfaces such as fins or other structures to which heat from coolant inside the integrated heat exchanger can be transferred, and then removed by a flow of air or other coolant from the fans 757. As a result of the integration of HTEX 772 and HTEX 704 together, a liquid-liquid heat transfer arrangement is implemented in which the pressure shell coolant removes heat from the coolant received by the HTEX 772 from the cooled equipment 475a.

E. Aspects of Example Pressure Shells

Figure 5A:
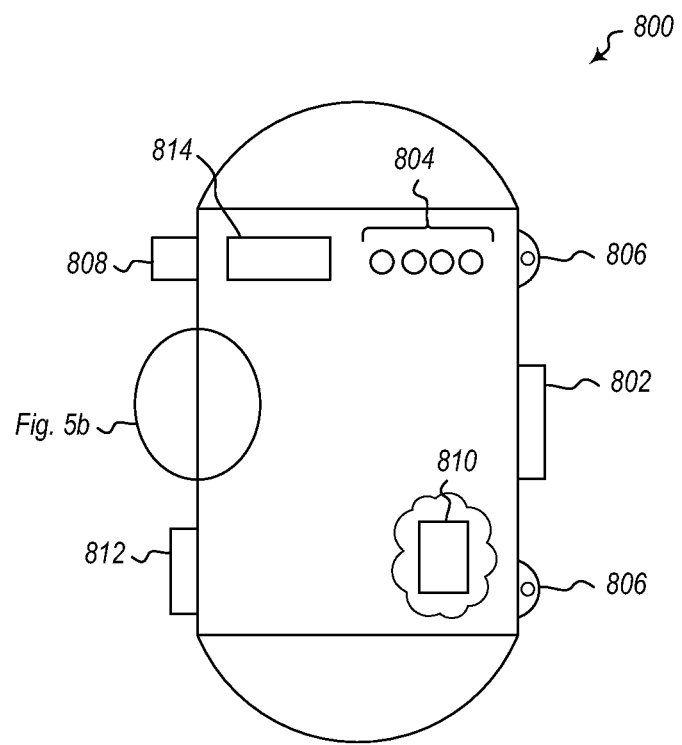
FIG. 5a discloses aspects of an example shell having an integrated heat exchanger.
Figure 5B:
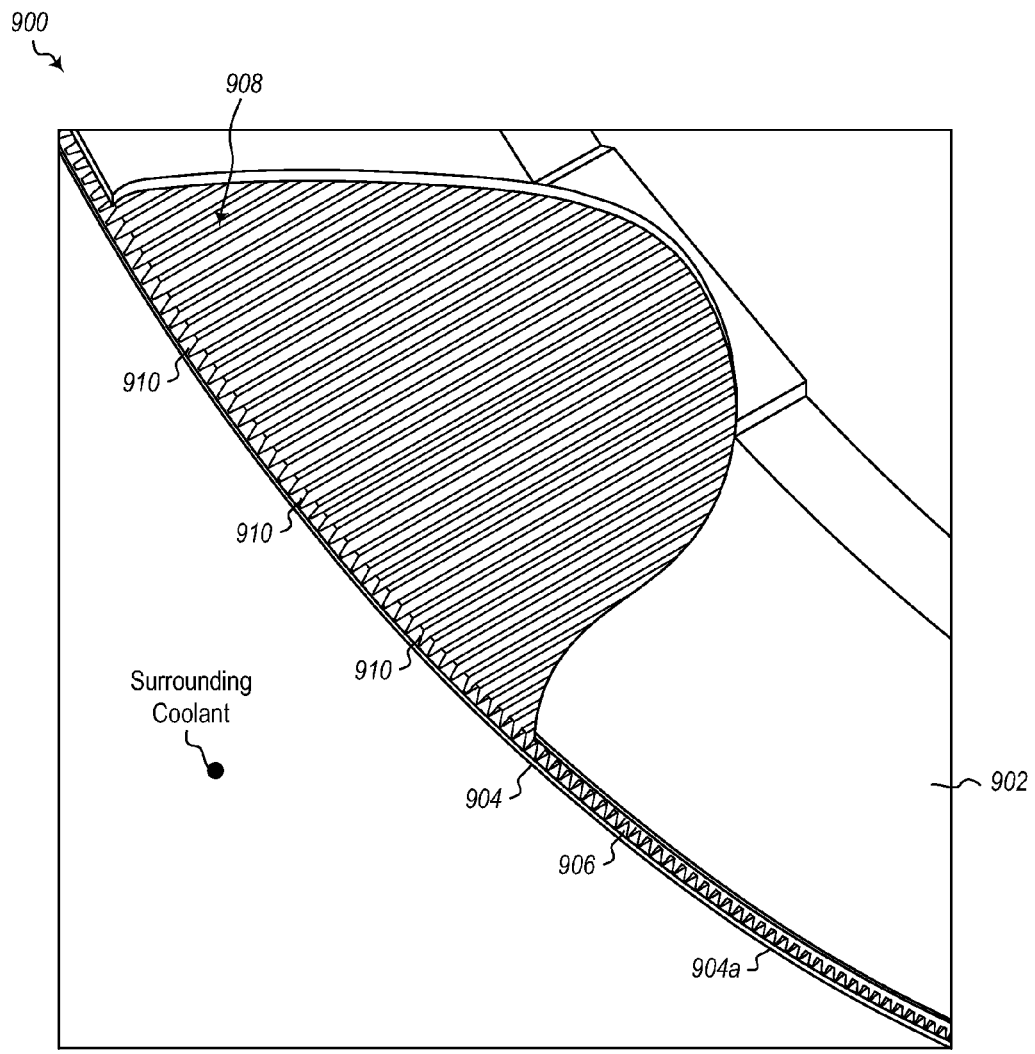
FIG. 5b discloses aspects of an example wall configuration that forms part of an integrated heat exchanger of a shell.

With reference now to FIGS. 5a-5e, details are provided concerning example embodiments of a pressure shell. In FIGS. 5a and 5b, one example embodiment of the pressure shell is denoted at 800. The example pressure shell 800 has a generally cylindrical shape with a domed top and bottom, although as noted herein, the pressure shell 800 can be any suitable size and shape and, accordingly, the embodiment of FIG. 5a is presented solely by way of example. The size and shape of the pressure shell 800 may also be determined at least in part based on the further considerations noted below. In one example embodiment, the pressure shell 800 is between about 7 feet and 9 feet in diameter, and one particular embodiment is about 8 feet in diameter. Larger, or smaller, lengths and/or diameters than those disclosed in the foregoing examples, as well as any other measurements, could also be employed, and the scope of the invention is not limited to any particular size or configuration of a pressure shell.

Electronic equipment, such as datacenter components for example, can be removably mounted on racks (not shown) inside the pressure shell 800. However, the scope of the invention does not require the use of racks, nor any other particular mounting equipment or arrangement. Thus, for example, the electronic equipment and/or racks can instead be hard mounted directly to the pressure shell 800, or can be resiliently mounted, such as with rubber-insert mounts for example, to reduce a noise signature associated with operations inside the pressure shell 800.

In terms of construction materials, the pressure shell 800 can be made of any material(s) suited to the environment in which it is expected to be used, such as seawater or freshwater. The depth to which the pressure shell 800 is expected to be immersed is also a consideration in material selection, as is the desired thermal conductance, that is, heat transfer performance, of the pressure shell 800. With these points in mind, example materials for the pressure shell include, but are not limited to, steel, carbon composites, aluminum, aluminum alloys, titanium, copper, and copper alloys including copper-nickel alloys (CNA). At least some of these materials, such as titanium and copper alloys, are resistant to corrosion and biofouling in seawater and freshwater.

The pressure shell 800 includes one or more removable access hatches 802 to enable access to components located in the interior space of the pressure shell 800. In some embodiments, removable access hatches can be omitted. The access hatches 802 can include any type of seals, one example of which is O-rings, to ensure a watertight seal of the interior space of the pressure shell 800 when the pressure shell 800 is partially or completely immersed. The access hatch(es) 802 can be sized, located, and oriented in the pressure shell 800 as necessary to suit access requirements.

In one particular embodiment, the access hatch 802 takes the form of a removable end plate, or cap, which can be domed or flat. In this example, the access hatch 802 is held in position, on a flange of the pressure shell 800 for example, with a ring of bolts and sealed with O-rings.

As further indicated in FIG. 5a, the pressure shell 800 may include one or more watertight shell penetrations 804 by way of which monitoring, power and control signals can be sent between the pressure shell 800 and a remote location. Thus, the shell penetrations 804 may accommodate, for example, wires, cables, optical fibers, plumbing connections, or combinations of these. Such signals, and associated signal carriers, can be associated with any aspect of the pressure shell 800 and related systems and components including, for example, electronic components located in the pressure shell 800, cooling systems for the electronic components, and the environment of the interior of the pressure shell 800. The plumbing connections can be for any system or device and can include, for example, a bilge pump discharge connection, and a pressure connection for the pressure shell such as could be used to evacuate and/or pressurize the interior of the pressure shell.

Other elements of the example pressure shell 800 include one or more lift points 806. In general, the lift points 806 include an eye or other structure that can accommodate a chain, cable, hook and/or other lifting devices. The lift points 806 can be used when immersing the pressure shell 800, when retrieving the pressure shell 800, and performing various other operations concerning the pressure shell 800 such as, but not limited to, manipulating the pressure shell 800 during assembly, shipping, mooring, service, or positioning on a seabed, foundation, or other underwater location. In some embodiments, lift points can be omitted and the pressure shell can include one or more hard points by way of which the pressure shell can be positioned and manipulated using straps, chains, or other devices.

When the pressure shell 800 is employed in seawater environments, additional considerations may come into play with regard to the overall design. For example, some embodiments of the pressure shell 800 may employ a cathodic protection system 808 that uses one or more sacrificial elements to prevent or reduce corrosion of the pressure shell 800 and/or its components. In another approach, where dissimilar metals are employed, non-corroding materials such as rubber or plastic can be used as an interface between those materials to eliminate, or at least reduce, corrosion in aggressive environments such as seawater.

As well, the pressure shell 800 may include environmental monitoring and control equipment 810 disposed within the pressure shell 800. Such environmental monitoring and control equipment 810 can facilitate the monitoring and control of environmental parameters such as temperature, pressure, noise, shock, vibration, volatile organic compounds (VOC), and humidity of the interior environment of the pressure shell 800. It should be noted that some humidity may be desirable to help reduce static. The temperature of the interior and exterior walls of the pressure shell 800 can also be monitored. The environmental monitoring and control equipment 810 can include, for example, one or more of cameras, sensors for any of the monitored parameters, as well as air heaters, dryers, air coolers, and desiccants. Where a relatively dry environment with low, or no, humidity is desired, equipment such as ionizers can be used to prevent buildup of static.

In connection with the foregoing, the environment inside the pressure shell 800 can include any suitable gas, or gases. Example gases include air, nitrogen, $CO_2$, nitrogen-rich environments, inert gases such as helium, and any combination of these. The pressure of the interior environment of the pressure shell 800 can be relatively low, such as less than about 2 atmospheres, and about 1 atmosphere (about 14.7 psi) in one particular embodiment.

As some further examples, fluids which may be used in the pressure shell interior environment suitable for operating temperatures within all or a portion of the temperature range of about −10C to about 120C, with atmospheric pressures ranging from about 0.1 standard atmospheres (10.1325) kPa to about 200 standard atmospheres (20.265 MPa) or a subset include, but are not limited to, dielectric fluids, liquid mineral oil, liquid or liquid/gas or supercritical propane, liquid or liquid/gas or supercritical pentane, liquid or liquid/gas or supercritical carbon dioxide, gas or supercritical helium or nitrogen, liquid or liquid/gas or supercritical alcohols including 2,2-dimethyl-1-propanol, azeotropes and any other combinations which include one or more of the preceding items.

In some instances, the pressure of the interior environment may be a function of the hydrostatic pressure on the exterior of the pressure shell 800. In any case, the pressure shell 800 can be employed at any suitable depth and, in some particular embodiments, the pressure shell 800 is employed at depths in a range of about 180 meters to about 220 meters, with one particular embodiment contemplated for use at a depth of about 200 meters. In some instances at least, the pressure shell 800 can be located at a depth that assures no collisions or other interference by divers, passing ships, or other structures or craft, but at the same time, a depth that is no deeper than necessary to avoid such problems, since significant depths would require relatively thicker walls in the pressure shell 800.

In addition to providing for monitoring and control of the interior environment of the pressure shell 800, provision can also be made for monitoring aspects of the surrounding environment in which the pressure shell 800 has been immersed. Accordingly, the example embodiment of FIG. 6a includes external environment monitoring equipment 812 that can be attached, directly or indirectly, to the exterior of the pressure shell 800, an external HTEX, or any other structure associated with the pressure shell 800. The external environment monitoring equipment 812 can include sensors for measuring and reporting concerning, for example, one or more of water temperature, hydrostatic water pressure and corresponding depth, flow rate, chemical attributes such as salinity, and changes in water pressure due to underwater events.

Further, some embodiments of the pressure shell 800 may include ultraviolet-C (UVC) lighting 814, such as one or more groups of UVC lamps for example, that can help to eliminate, or at least reduce, biofouling of the external heat exchangers and/or other components on the exterior of the pressure shell 800. Any other germicidal lighting and/or techniques could additionally, or alternatively, be employed however. As one example, ultrasonic agitation equipment and processes can be used for anti-fouling and/or de-fouling. It will be appreciated that UVC equipment and ultrasonic agitation equipment are example structural implementations of a means for performing anti-fouling and/or de-fouling. More generally, any other system(s) and/or equipment configured to perform one or both of these functions can alternatively be employed.

F. Aspects of Example Pressure Shell Wall Configurations

Directing attention now to FIGS. 5b-5e, details are provided concerning example pressure shell wall configurations that include an integrated heat exchanger. In the example of FIGS. 5b-5e, the pressure shell is designated generally at 900.

As indicated in the Figures, the pressure shell 900 includes an interior wall 902 that is spaced apart from an exterior wall 904 so that a space 906 is collectively defined by, and between, the interior wall 902 and exterior wall 904. An outer surface 904a of the exterior wall 904 is exposed to the surrounding environment, such as water, when the pressure shell 900 is in use.

In at least one embodiment, a corrugated layer 908, such as corrugated metal stock for example, is positioned in the space 906. More specifically, the corrugated layer is attached to the interior wall 902 and then the exterior wall 904, which serves as a cap, is then attached to the corrugated layer 908 and/or the interior wall 902. In this way, fluid passageways are defined on both sides of the corrugated layer 908. Alternatively, the corrugated layer 908 could first be attached to the inner surface of the exterior wall 904, and then the resulting assembly attached to the outer surface of the interior wall 902.

The corrugated layer 908 can be welded, soldered, brazed, vacuum brazed, or otherwise attached, such as by way of a thermal epoxy for example, to one or both of the interior wall 902 and exterior wall 904. One alternative to these is shrink fitting the interior wall 902 and exterior wall 904 via thermal differences thereby trapping the corrugated layer 908 between and providing high contact pressure needed for good heat transfer.

The corrugated layer 908 can be made of any material(s) compatible with the coolant, which can be liquid or gas, to be employed. In some embodiments, the corrugated layer 908 is made of the same, or similar, materials as the interior wall 902 and exterior wall 904. As well, the corrugated layer 908 can be relatively thinner or thicker than the interior wall 902 and/or the exterior wall 904.

Thus configured and arranged, the corrugated layer 908 cooperates with the interior wall 902 and exterior wall 904 to define multiple fluid passageways 910, on each side of the corrugated layer 908, that serve to direct a flow of coolant, as discussed elsewhere herein. More particularly, heated coolant circulating through the fluid passageways 910 transfers heat to the exterior wall 904 and then to the surrounding coolant. Depending upon the configuration, all of the fluid passageways 910 are in fluid communication with each other in some embodiments while, in other embodiments, some or all of the fluid passageways 910 are isolated from other fluid passageways 910. As the foregoing thus makes clear, the interior wall 902, exterior wall 904, and corrugated layer 908 cooperatively define at least part of a heat exchanger that is integrated into the pressure shell 900 itself.

It will be apparent that the structure of the corrugated layer 908 is such that the corrugated layer 908 possesses a number of attributes that make it well suited for use in heat transfer applications. For example, the corrugated structure provides a relatively large surface area. Inasmuch as the rate of heat transfer is a function of surface area, relatively greater heat transfer rates can be achieved with the corrugated layer 908 than would be possible if the corrugated layer 908 were flat, or not present at all.

As one alternative to a corrugated layer, a layer incorporating a pin fin configuration could be used. One example of a pin fin layer is a substantially flat piece of material that includes a plurality of surfaces, such as pins, extending outward from at least one surface of the material. The pins, or other extended surfaces, could be oriented toward the interior wall 902 or toward the exterior wall 904. In yet another alternative embodiment, a pair of pin fin layers could be arranged back-to-back, that is, with the pins of the respective layers extending in opposite respective directions.

The back-to-back pin fin layers could be positioned between the interior wall 902 and the exterior wall 904.

The specific size and configuration of the corrugated layer 908 can be selected based on a number of parameters. Such parameters can include feasibility of manufacture, acceptable coolant pressure loss through the fluid passageways 910 associated with the corrugated layer 908, and a desired coolant flow rate through the fluid passageways 910. A variation of the corrugated layer 908 that implements the same functionality could be a mesh or an upset and punched sheet metal screen. Either of these also provide a large surface area with which to transfer heat from the coolant fluid to the exterior wall of the pressure vessel.

Figure 5C:
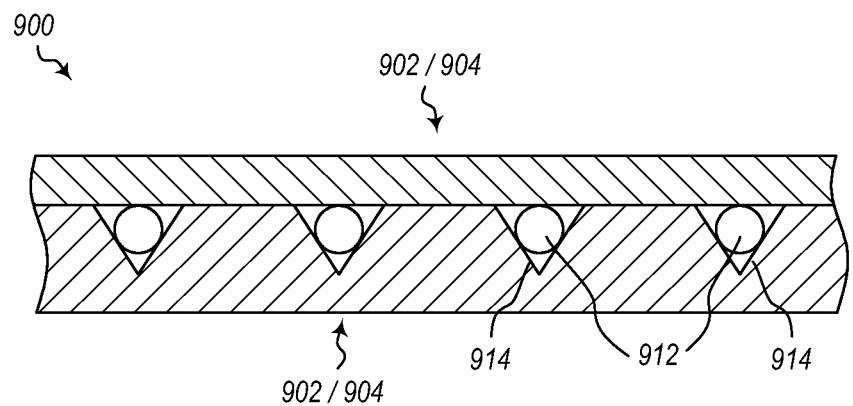
FIG. 5c discloses aspects of an alternative wall configuration that forms part of an integrated heat exchanger of a shell.

In addition to the example set forth in FIG. 5b, and with reference to FIG. 5c, a number of variations are possible. For example, rather than employing a separate corrugated layer 908, a series of grooves 914 can be formed on an inner surface of the exterior wall 904 and/or on the outer surface of the interior wall 902. The grooves 914 thus formed cooperate with a surface of the other wall to define a plurality of fluid passageways. The grooves 914 can be formed in any suitable manner, and example processes for forming the grooves include, but are not limited to, milling, skiving, forging, chemical etching, or any combination of these. In some embodiments, the grooves 914 are formed by rolling the base material with dies. Where the grooves 914 are formed directly into the exterior wall 904 or interior wall 902, those wall materials may be relatively thicker than in the case where a separate corrugated layer is employed, since the walls have to maintain a minimum thickness after the grooves 914 are created.

In yet another alternative shown in FIG. 5c, a series of tubes 912, which could be in a serpentine form or a series of loops, can be positioned between the interior wall 902 and exterior wall 904. In a variation of this alternative, both tubes 912 and grooves 914 could be employed, with the tubes 912 being pressed into respective grooves 914, such that the tubes 912 and grooves 914 are both positioned between the interior wall 902 and the exterior wall 904. The tubes 912 can be the same, or similar, materials as the interior wall 902 and/or the exterior wall 904, and the grooves 914 can be formed in either of the interior wall 902 or exterior wall 904. In yet another variation on the arrangement of FIG. 5c, only the wall that includes the grooves 914 is employed and the other wall that covers the grooves 914 is omitted. In this variation, the tubes 912 can be included in the grooves 914.

The tubes 912 are not employed in all embodiments and, in some instances, only grooves 914 are used. Thus, where only grooves 914 are employed, the coolant flowing in the grooves 914 can directly contact both the interior wall 902 and exterior wall 904 while, in the embodiments that employ tubes 912, the coolant flows within the tubes 912 and, as such, does not directly contact either of the interior wall 902 or the exterior wall 904. However, effective heat transfer to the exterior wall 904 can nonetheless be achieved by virtue of the contact between the tubes 912 and the exterior wall 904.

Figure 5D:
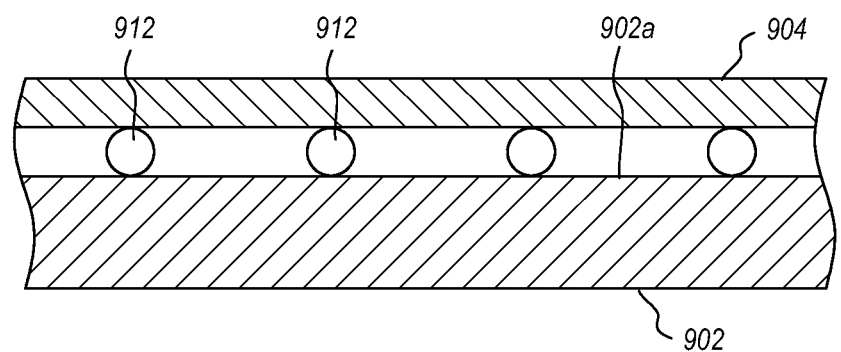
FIG. 5d discloses aspects of a configuration where fluid passageways are provided on the exterior of the shell and then capped with a cap layer or exterior wall.

In the embodiment of FIG. 5d, the interior wall 902 of the pressure shell is relatively thick and includes a group of tubes 912 disposed on the outer surface 902a of the interior wall 902. In this embodiment, the interior wall 902 provides the strength and structural integrity of the associated pressure shell. The tubes 912 can be attached to the outer surface 902a by any of the methods disclosed herein. The exterior wall 904, which is relatively thinner than the interior wall 902, serves as a cap layer over the tubes 912. While the exterior wall 904 is relatively thin, it is supported by the relatively thick interior wall 902. In one illustrative embodiment, the interior wall 902 could be made of steel and have a thickness in a range of about ¾" to about 1", and the exterior wall 904 or cap layer could have a thickness in a range of about ⅛" to about ¼". In one alternative to this particular embodiment, the tubes 912 could be omitted and grooves can be formed in the outer surface 902a to serve as fluid passageways when capped by the exterior wall 904. In yet another alternative, the tubes 912 could be omitted and replaced with a corrugated layer, mesh, or screen to provide fluid passageways when capped by the exterior wall 904. As in the case of other corrugated layers disclosed herein, the pitch of such a corrugated layer could be in a range of about ⅛" to about ¼", although any other pitch could be used for any of the disclosed embodiments of a corrugated layer. In similar fashion, the thickness and/or other attributes of the 'corrugated layer' and exterior wall can also vary from one embodiment to another.

An alternative embodiment to FIGS. 5c and 5d is to have tubes placed integrally within a cast pressure vessel wall (see, e.g., FIG. 7). That is, the tubes would be positioned prior to casting, and then the wall would be cast such that the casting material would flow around the tubes. Thus, when the casting was complete, the tubes would be positioned within the newly cast wall. In this example, there would only be a single pressure vessel wall. The tubes in this embodiment could collectively form series and/or parallel cooling loops. In a further variation of this embodiment, tubes need not be employed. For example, ceramic rods or other structures could be positioned in a casting mold and then removed after casting, leaving a series of tubes integrally formed within the cast wall.

In any of the embodiments disclosed herein, the fluid passageways, regardless of their form and configuration, can be oriented with respect to the associated pressure shell in any desired manner. By way of example, in some embodiments, one, some or all of the fluid passageways are oriented generally radially about the pressure shell. In another example, one, some or all of the fluid passageways are oriented generally longitudinally, or parallel to a longitudinal axis defined by the pressure shell. As a final illustrative example, the fluid passageways 910 indicated in FIG. 5b are shown as axially oriented relative to a longitudinal axis of a shell, but those fluid passageways could alternatively be radially oriented relative to a longitudinal axis of the shell. In this latter configuration, the fluid passageways would be substantially perpendicular to the indicated orientation. Any other orientation of the fluid passageways can alternatively be implemented as well. The fluid passageways in any scheme may be of any size necessary to achieve the desired performance. Thus, the fluid passageways may conform to dimensions associated with micro-channels, mini-channels, and macro-channels.

In any of the embodiments disclosed herein, the exterior surface of the pressure vessel wall may have features to enhance the transfer of heat from within. These features may include but are not limited to: fins, roughness, dimples, or any means necessary to increase surface area and or turbulence of the flow of the surrounding external fluid environment.

Figure 5E:
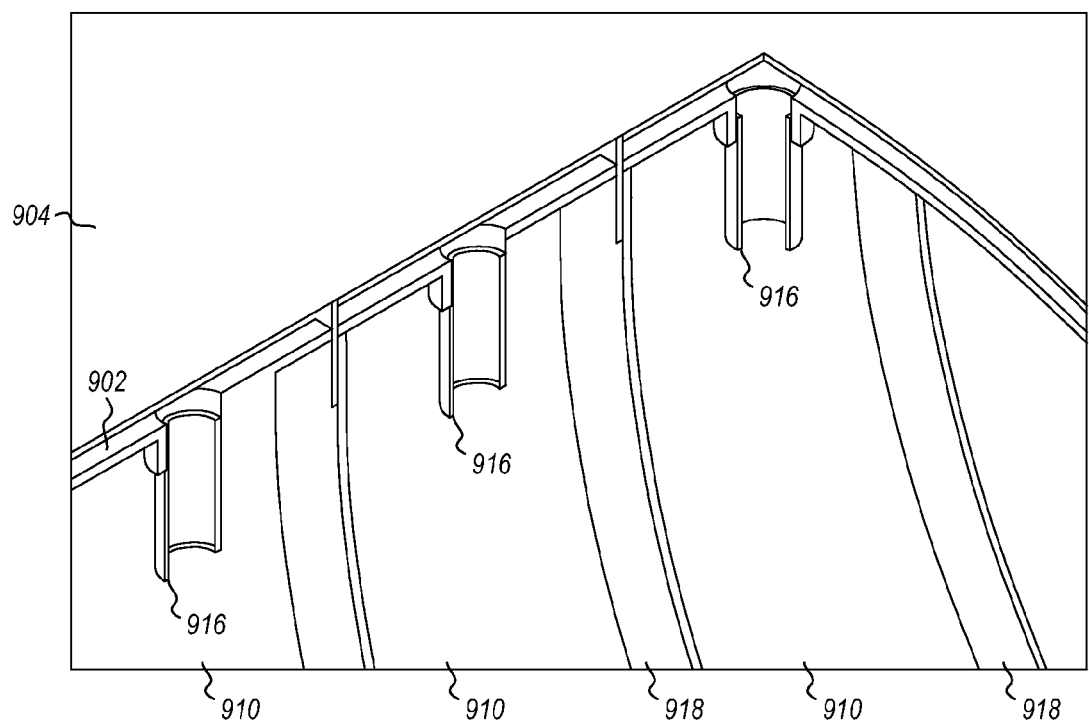
FIG. 5e discloses further aspects of an example integrated heat exchanger of a shell.

With continued attention to FIG. 5a-5d, and directing particular attention now to FIG. 5e, further details are provided concerning an arrangement for directing coolant flow to and from a series of fluid passageways disposed in a pressure shell. In the illustrative example of FIG. 5e, a series of manifold connections 916 are provided that are each in fluid communication with one or more fluid passageways 910. The manifold connections 916 can be welded, brazed, soldered, or otherwise attached to the interior wall 902, and the manifold connections 916 serve as entry and exit points, depending upon their location, to the fluid passageways 910. Thus, heated coolant can enter the fluid passageways 910 by way of one group of manifold connections 916 and then, after cooling, the coolant can exit the fluid passageways 910 by another group of manifold connections 916. An entry manifold connection 916 and exit manifold connection 916 can be provided for each fluid passageway 910 or, alternatively, a single entry manifold connection 916 can be provided for a group of fluid passageways 910, and a single exit manifold connection 916 can be provided for that group of fluid passageways 910. Thus, in some embodiments, all of the fluid passageways 910 are in fluid communication with each other while, in other embodiments, some fluid passageways 910 are isolated from other fluid passageways 910.

It should be noted with respect to the embodiment of FIG. 5e that the fluid passageways 910 are defined at least in part by a series of ribs 918 that are connected to the interior wall 902. Such ribs 918, which can be included inside and/or outside the pressure shell, may be included in some pressure shell configurations in order to provide strength and structural integrity, while also enabling the interior wall 902 and/or exterior wall 904 to be relatively thinner than would be the case if the ribs 918 were omitted.

With reference now to FIG. 6, details are provided concerning some example external configurations of shells, such as pressure shells. In general, and as indicated in the particular examples of FIG. 6, shells such as are disclosed herein may include extended surfaces on their exterior walls. Because the extended surfaces are arranged for thermal communication with the surrounding environment, the extended surfaces increase the surface area of the exterior of the shell and thereby help to improve heat transfer from the shell to the surrounding environment. As discussed below, such extended surfaces can be implemented in a variety of ways and, accordingly, the particular embodiments noted here are presented only by way of illustration and are not intended to limit the scope of the invention in any way.

In one example embodiment, a shell 950 is provided that, except as noted below, may be similar, or identical, to any of the shells disclosed herein. The shell 950 includes a plurality of extended surfaces 952. The extended surfaces 952 can be made of any materials that are good thermal conductors, such as metals for example. The extended surfaces 952 have a solid construction and can be attached to the shell 950 in any suitable manner, examples of which include welding, soldering and brazing. Where the shell 950 is of cast construction, the extended surfaces 952 may be integrally formed with the shell 950. One useful aspect of the aforementioned extended surfaces 952 is that they do not necessitate any penetrations of the shell 950.

The extended surfaces 952 can have a variety of configurations. For example, the extended surfaces 952 can take the form of a plurality of pin fins as shown in the example of FIG. 6. The use of pin fins as extended surfaces of 952 may be especially well suited in circumstances where the shell 950 is expected to encounter random current flow. As another example, the extended surfaces 952 can take the form of a series of radial annular fins. In still another example, a single extended surface 952 is provided that takes the form of a single spiral structure. Of course, multiple different configurations of extended surfaces 952 can be combined in a single shell 950.

With continued reference to FIG. 6, another embodiment of a shell is disclosed and denoted generally at 970. Except as noted below, the shell 970 may be similar, or identical, to the shell 950 or to any other shell disclosed herein. As indicated in FIG. 6, the shell 970 may include a plurality of extended surfaces 972. Unlike the extended surfaces 952 however, the extended surfaces 972 are not solid and, instead, each define respective internal fluid passageways 974, such as micro-channels for example, through which a coolant is able to flow. The fluid passageways 974 are in fluid communication with the fluid passageways 976 that are included as elements of an integrated heat exchanger. Thus, a number of shell penetrations would be required to permit fluid communication between the fluid passageways 974 of the extended surfaces 952, and the fluid passageways 976.

With continued reference to FIG. 6, a further embodiment of a shell involves the use of extended surfaces and heat pipes. Except as noted below, the discussion of the other two embodiments of FIG. 6 applies as well to this final example embodiment.

In this final example embodiment of FIG. 6, the exterior of a shell 980 may include a plurality of extended surfaces 982 that extend away from the shell 980 and are arranged for contact with the surrounding environment. The extended surfaces 982 may, but need not, all have the same size, configuration and/or orientation as each other. In the illustrated example, the extended surfaces 982 take the form of a series of annular fins disposed about the circumference of the shell 980, but as noted above in the discussion of the other embodiments of FIG. 6, any other configuration and arrangement of extended surfaces 982 could alternatively be employed, and the use of a series of annular fins is presented only by way of illustration. As another example, each of the extended surfaces 982 could take the form of a pin fin.

In this particular embodiment, one or more extended surfaces 982 are in the form of a heat pipe 984, which could be a pin fin or any other shape or configuration. The heat pipes 984 are attached to the exterior of the shell 980 in any manner that will provide good thermal communication between the shell 980 and the heat pipe 984. For example, the heat pipes 984 could be attached to the shell 980 by brazing or soldering. As well, the heat pipes 984 can be made of any material that provides good heat transfer while also being resistant to biofouling and/or other problems that may be presented by the surrounding environment in which the shell 980 is disposed when in use. Examples of such heat pipe 984 construction materials include copper and copper alloys such as copper-nickel, but other materials could be used as well.

In terms of their location, the heat pipes 984 may be located anywhere relative to the shell 980 that the heat pipes 984 are able to transfer heat away from the shell 980. For example, the heat pipes 984 may be located only on a portion, such as an upper portion, or upper half, of the shell 980. One example of this is the arrangement indicated in FIG. 6. In other embodiments however, the heat pipes 984 may extend, or be provided, along a majority, or the full length, of a height or other dimension of the shell 980. More generally, the scope of the invention is not limited to any particular number, placement, or orientation, of heat pipes 984. As well, one or more heat pipes 984 can be combined together in a single embodiment with any one or more of the other extended surfaces disclosed herein, including the other examples of FIG. 6.

Each of the heat pipes 984 includes a volume of coolant disposed at the bottom of the heat pipe 984, which is typically located near a heat source such as the shell 980. In general, each heat pipe 984 is a closed system that is not in fluid communication with any other components. Thus, the coolant in the heat pipe 984 remains in the heat pipe 984 at all times during normal operations.

When no significant heat is being generated by the heat source, such as the shell 980 for example, the coolant in each of the heat pipes 984 is generally in a liquid form. When the heat source is generating significant heat, the coolant in the heat pipes 984 boils, thereby removing at least some of the generated heat. The vaporized coolant moves away from the heat source, such as upward in the heat pipes 984, where the surfaces of the heat pipe 984 are relatively cooler, as a result of being relatively remote from the heat source. The vaporized coolant condenses when it contacts the relatively cooler surfaces of the heat pipe 984, and the now-liquid coolant falls to the bottom of the heat pipe 984, and the cycle is repeated.

Turning now to FIG. 7, details are provided concerning some further example arrangements of cooled equipment relative to an integrated heat exchanger. In the particular examples of FIG. 7, the cooled equipment 1000 is in the form of one or more chips, such as integrated circuit (IC) chips for example. However, the scope of the invention is not so limited, and any other cooled equipment, such as circuitry, chips, or devices, could be arranged as shown in FIG. 7. As indicated, the cooled equipment 1000 can be directly attached to the interior wall 902 so that heat generated by the cooled equipment 1000 is transferred by conduction to the interior wall 902, and then to coolant flowing in fluid passageways that contact the interior wall 902. More generally, cooled equipment 1000 can be directly attached to the interior wall of any of the embodiments disclosed herein, including the interior wall 902 of FIG. 5b.

With continued reference to FIG. 7, the cooled equipment 1000 can be employed in connection with various embodiments of a shell 900 that have a single wall configuration. In one particular example, the shell 900 includes only the exterior wall 904. As indicated in that example, the exterior wall 904 defines a plurality of grooves 914 in which are disposed tubes 912 that define fluid passageways. The cooled equipment 1000 can be mounted directly over the tubes 912, as shown, although that is not necessarily required. Thus, in some embodiments, the cooled equipment 1000 can be mounted to the exterior wall 904 in a location near, but not over, the tubes 912.

As also shown in FIG. 7, the cooled equipment 1000 can be employed with a shell 900 having another type of single wall construction. In this example, the tubes 912 are located within the structure of the exterior wall 904. As noted elsewhere herein, this configuration can be achieved, for example, by casting the exterior wall 904 with the tubes 912 arranged in such a way that they reside within the exterior wall 904 after casting is complete. The cooled equipment 1000 can then be mounted directly to the exterior wall 904 as shown.

The scope of the invention is not limited to any particular method or mechanism of attaching cooled equipment 1000 to a wall of a shell that includes an integrated heat exchanger. Rather, the cooled equipment 1000 can be attached in any suitable way so long as provision is made for substantial thermal communication, such as by way of extensive physical contact, between the cooled equipment 1000 and the interior wall 902. Some attachment methods could include soldering, brazing, and the use of thermally conductive adhesives. In some embodiments, the cooled equipment 1000 can be removably attached so as to allow, for example, for maintenance or replacement of the cooled equipment 1000. It should be noted that, as disclosed herein, some embodiments of the shell have only a single wall, with an interior surface of the wall serving as a mounting location for the cooled equipment 1000, and the exterior surface of the wall in contact with the surrounding environment.

With reference now to FIG. 8, it will be appreciated that the arrangement of the pressure shell itself relative to the surrounding environment can facilitate useful heat transfer effects. For example, where a pressure shell is disposed in still water, the cooling of external structures such as the wall of the pressure shell occurs both by conduction and by natural convection. The natural convection can create an upward, that is, against gravity, flow of water outside the pressure shell. It can thus be desirable to arrange the direction of coolant flows in the integrated heat exchanger to be in a downward direction, that is, in a direction opposite the direction of the flow of surrounding fluid that is imparted by natural convection. In this way, a counter flow effect is achieved that may provide relatively better heat transfer relative to arrangements where a cross flow or parallel flow configuration is employed.

In particular, and as shown in FIG. 8, a shell 1050 includes a coolant pump 1052, or other prime mover, that discharges a flow of heated coolant into fluid passageways 1054 integrated into the shell 1050. As the heated coolant flows from the top of the shell 1050 down to the bottom of the shell 1050, heat is removed from the coolant by virtue of its thermal communication with the shell 1050, and the thermal communication between the shell 1050 and the surrounding environment.

As a result of the rejection of heat from the coolant to the surrounding environment, some of the fluid in the surrounding environment is heated. Thus, a natural convection process takes place in which this heated fluid flows upward, that is, in a direction opposite the gravitational force, and opposite the direction of flow of the coolant in the fluid passageways 1054. Thus, a counter flow effect is achieved that contributes to an overall improvement in the heat transfer performance associated with the shell 1050.

G. Aspects of Example Production Methods

Figure 9:
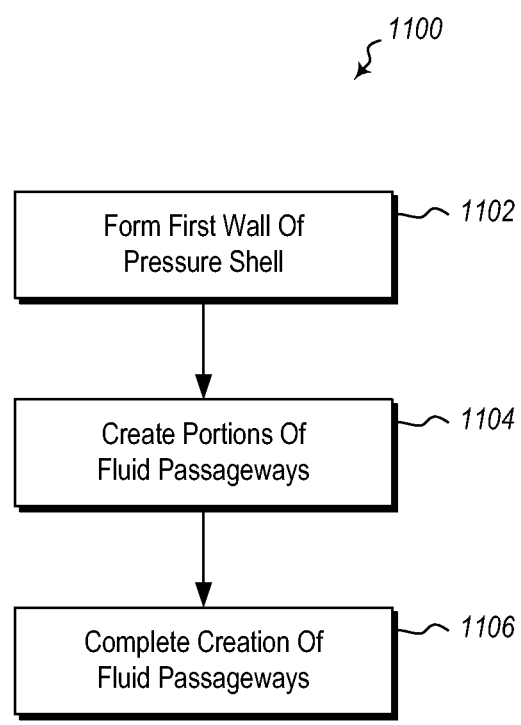
FIG. 9 is a flow diagram indicating an example process for manufacturing an example shell with an integrated heat exchanger.

With attention finally to FIG. 9, details are provided concerning example methods for making a pressure shell with an integrated heat exchanger. The example method of FIG. 9 is denoted generally at 1100. At 1102, a first wall of the pressure shell is formed. This first wall can be an interior wall or exterior wall of the pressure shell, and may comprise one or more sheets of metal, examples of which are disclosed herein, and which can be attached to each other by welding, brazing, soldering or other suitable processes. In other embodiments, and depending upon the composition of the wall, formation of the first wall may involve laying up one or more layers of a composite material on or in a mold. Next, at least portions of one or more fluid passageways are defined 1104. As noted herein, this process can involve creation of grooves in the interior and/or exterior walls and, in some embodiments, the placement of tubes in the grooves. This process 1104 can alternatively involve attachment of a corrugated layer to one of the interior wall or exterior wall of the pressure shell.

At 1106, creation of the fluid passageways is completed. This can be accomplished, for example, by placing a cap layer, such as an exterior wall for example, over the partially completed fluid passageways. The cap layer cooperates with the exposed grooves, for example, to enclose any open grooves and thereby form completed fluid passageways in the wall of the pressure shell.

After 1106, has been completed, at least part of a heat exchanger has been integrated into the pressure shell. Additional processes can include placement of manifold connections, attaching domes or other caps to the pressure shell, and placing equipment within an interior of the pressure shell.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A portion of a submersible pressure shell, comprising:
    a shell wall portion that includes:
        an interior wall portion;
        an exterior wall portion located proximate the interior wall portion;
        a corrugated layer positioned between the interior wall portion and the exterior wall portion, the corrugated layer comprising alternating angular ridges and angular grooves; and
    a plurality of fluid passageways disposed between the interior wall portion and the exterior wall portion, within at least some of the angular grooves of the corrugated layer;
    wherein at least some of the fluid passage ways are in direct contact with the interior wall portion and at least some of the fluid passageways are in direct contact with the exterior wall portion.

2. The portion of a shell as recited in claim 1, wherein the fluid passageways comprise grooves formed in one or both of the interior wall portion and the exterior wall portion.

3. The portion of a shell as recited in claim 2, further comprising a plurality of tubes, a portion of a tube being positioned in a corresponding groove.

4. The portion of a shell as recited in claim 1, wherein the interior wall portion and the exterior wall portion are spaced apart a distance from each other.

5. The portion of a shell as recited in claim 1, wherein the fluid passageways are isolated from an exterior of the shell portion such that, in use, fluid communication between the fluid passageways and a surrounding environment of the shell portion is prevented.

6. The portion of a shell as recited in claim 1, wherein, in use, a coolant in the fluid passageways directly contacts the exterior wall portion.

7. The portion of a shell as recited in claim 1, wherein the fluid passageways are cooperatively defined by the corrugated layer portion and one or both of the interior wall portion, and the exterior wall portion.

8. The portion of a shell as recited in claim 7, wherein some of the fluid passageways are located on a first side of the corrugated layer portion, and other fluid passageways are located on a second side of the corrugated layer portion, the second side of the corrugated layer portion being positioned opposite the first side of the corrugated layer portion.

9. The portion of a shell as recited in claim 1, wherein the portion of a shell is a portion of a pressure shell.

10. The portion of a shell as recited in claim 1, wherein the portion of a shell is a portion of a submersible shell.

11. A submersible pressure shell, comprising:
    an interior wall that partly defines an interior space of the submersible pressure shell, and an exterior wall located proximate the interior wall; and
    an integrated heat exchanger, including:
        a portion of the interior wall;
        a portion of the exterior wall; and
        a plurality of fluid passageways disposed between the interior wall and the exterior wall, wherein at least some of the plurality of fluid passageways comprise one or more tubes that are in direct contact with both an external surface of the portion of the interior wall and an internal surface of the portion of the wall.

12. The submersible pressure shell as recited in claim 11, wherein the integrated heat exchanger is configured and arranged such that coolant present in the fluid passageways directly contacts the exterior wall.

13. The submersible pressure shell as recited in claim 11, wherein the fluid passageways are isolated from an exterior of the submersible pressure shell such that, in use, fluid communication between the fluid passageways and a surrounding environment of the submersible pressure shell is prevented.

14. The submersible pressure shell as recited in claim 11, wherein the fluid passageways comprise grooves formed in one or both of the interior wall portion and the exterior wall portion.

15. The submersible pressure shell as recited in claim 11, wherein the fluid passageways are defined in part by a portion of a corrugated layer positioned between or including the portion of the interior wall and the portion of the exterior wall.

16. The submersible pressure shell as recited in claim 11, wherein the fluid passageways are isolated from fluid communication with the interior space of the submersible pressure shell.

17. The submersible pressure shell as recited in claim 11, further comprising a heat generating component disposed within the interior space of the submersible pressure shell.

18. The submersible pressure shell as recited in claim 17, further comprising a prime mover configured to direct a flow of coolant into thermal communication with the heat generating component and into the fluid passageways.

19. The submersible pressure shell as recited in claim 17, further comprising:
    a coolant pump in fluid communication with the fluid passageways;
    an air-fluid heat exchanger in fluid communication with the coolant pump; and
    a fan configured and arranged to direct a flow of gas into thermal communication with the air-fluid heat exchanger.

20. The submersible pressure shell as recited in claim 17, wherein the heat generating equipment is mounted directly to the interior wall portion.

21. The submersible pressure shell as recited in claim 11, further comprising one or more sensors configured to communicate with a remote location by way of a communication line extending out of the interior space of the submersible pressure shell, one of the sensors configured to perform one of: monitor and report on the datacenter component; monitor and report on an atmosphere inside the interior space of the submersible pressure shell; monitor and report on an atmosphere external to the submersible pressure shell; or, enable control of an aspect of the operation of one of the internal heat exchanger, the external heat exchanger, or the prime mover.

22. The submersible pressure shell as recited in claim 11, wherein the submersible pressure shell is substantially watertight over a range of immersion depths.

23. The submersible pressure shell as recited in claim 11, further comprising means for performing anti-fouling and/or de-fouling.

24. The submersible pressure shell as recited in claim 11, wherein the exterior wall includes a plurality of extended surfaces arranged for thermal communication with a surrounding environment.

25. The submersible pressure shell as recited in claim 24, wherein one or more of the extended surfaces includes an internal fluid passageway that is in fluid communication with one or more fluid passageways of the integrated heat exchanger.

26. The submersible pressure shell as recited in claim 24, wherein one or more of the extended surfaces is in the form of a heat pipe.

27. A portion of a shell, comprising:
 a shell wall portion that includes:
  an interior wall portion;
  an exterior wall portion located proximate the interior wall portion;
  a corrugated layer portion disposed between, and in contact with, the interior wall portion and the exterior wall portion, and
  a plurality of fluid passageways disposed between the interior wall portion and the exterior wall portion, wherein the fluid passageways are cooperatively defined by the corrugated layer portion and one or both of the interior wall portion, and the exterior wall portion, wherein some of the fluid passageways are located on a first side of the corrugated layer portion, and other fluid passageways are located on a second side of the corrugated layer portion, the second side of the corrugated layer portion being positioned opposite the first side of the corrugated layer portion.

28. The shell as recited in claim 27, further comprising heat generating equipment mounted directly to the interior wall portion.

* * * * *